(12) United States Patent
Spenser

(10) Patent No.: US 8,408,214 B2
(45) Date of Patent: Apr. 2, 2013

(54) METHOD FOR IMPLANTING PROSTHETIC VALVE

(76) Inventor: Benjamin Spenser, Bat Shlomo (IL)

( * ) Notice: Subject to any disclaimer, the term of this patent is extended or adjusted under 35 U.S.C. 154(b) by 179 days.

(21) Appl. No.: 12/803,849

(22) Filed: Jul. 8, 2010

(65) Prior Publication Data

US 2012/0010700 A1  Jan. 12, 2012

(51) Int. Cl.
 *A61B 19/00* (2006.01)
 *A61F 2/24* (2006.01)
(52) U.S. Cl. ........................ 128/898; 623/2.17
(58) Field of Classification Search ........................ None
See application file for complete search history.

(56) References Cited

U.S. PATENT DOCUMENTS

| | | | |
|---|---|---|---|
| 5,411,552 A | 5/1995 | Andersen et al. | |
| 5,840,081 A | 11/1998 | Andersen et al. | |
| 6,168,614 B1 | 1/2001 | Andersen et al. | |
| 6,730,118 B2 | 5/2004 | Spenser et al. | |
| 7,510,575 B2 | 3/2009 | Spenser et al. | |
| 7,611,534 B2 | 11/2009 | Kapadia et al. | |
| 7,618,446 B2 | 11/2009 | Andersen et al. | |
| 2004/0092858 A1* | 5/2004 | Wilson et al. | 604/9 |
| 2007/0050014 A1* | 3/2007 | Johnson | 623/1.24 |
| 2008/0140189 A1* | 6/2008 | Nguyen et al. | 623/2.11 |

FOREIGN PATENT DOCUMENTS

WO  WO 98/29057  7/1998

* cited by examiner

*Primary Examiner* — Thomas J Sweet
*Assistant Examiner* — Rebecca Preston

(57) ABSTRACT

A method for implanting a prosthetic valve apparatus in a novel location which replaces the function of a native diseased valve. The prosthetic valve apparatus includes a one way valve and an expandable valve seating. anchoring and securing apparatus in a newly created orifice near or at the center of the anterior valve leaflet. The prosthetic valve apparatus also causes the sealing of the native valve and thus results in a solution for paravalvular leakage and regurgitation.

21 Claims, 20 Drawing Sheets

Fig. 2
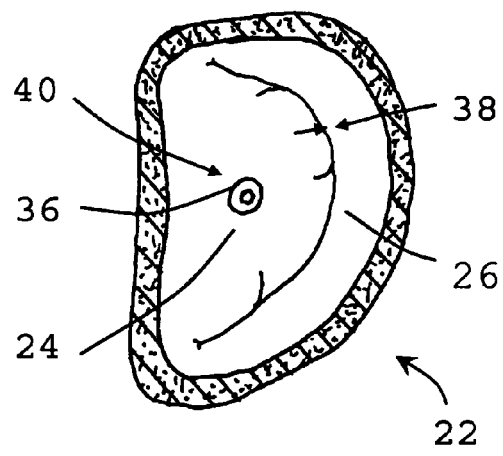
Fig 2a
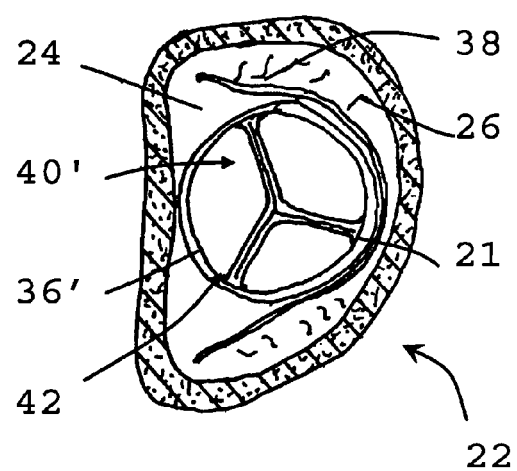
Fig 2b

Fig 3a             Fig 3b

Fig. 10
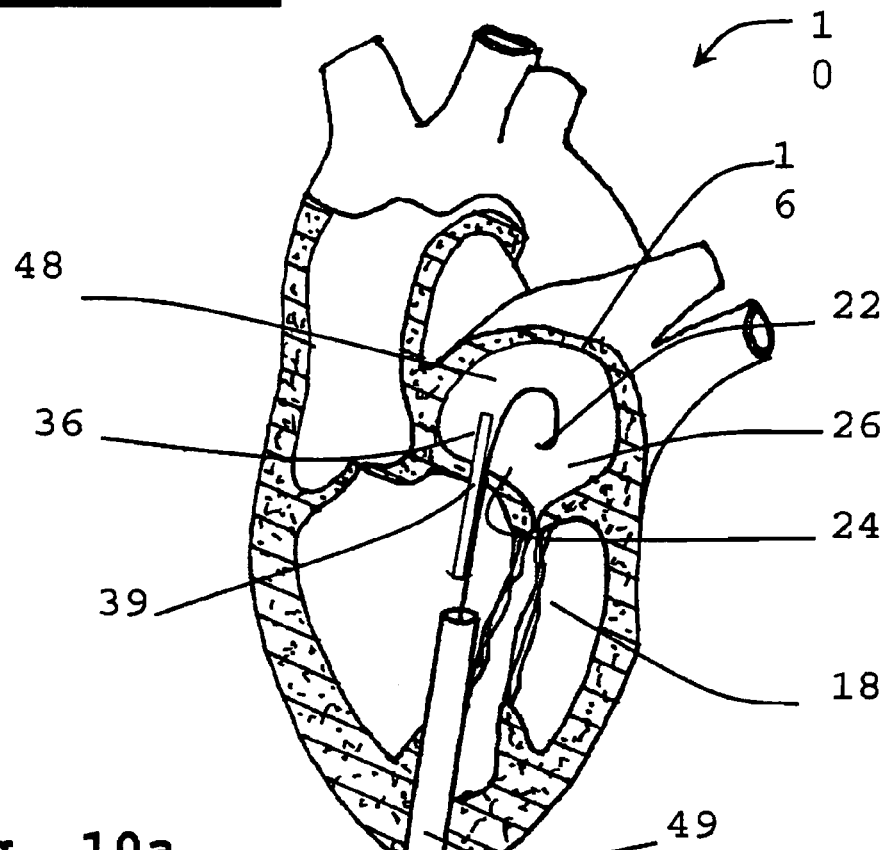
Fig. 10a
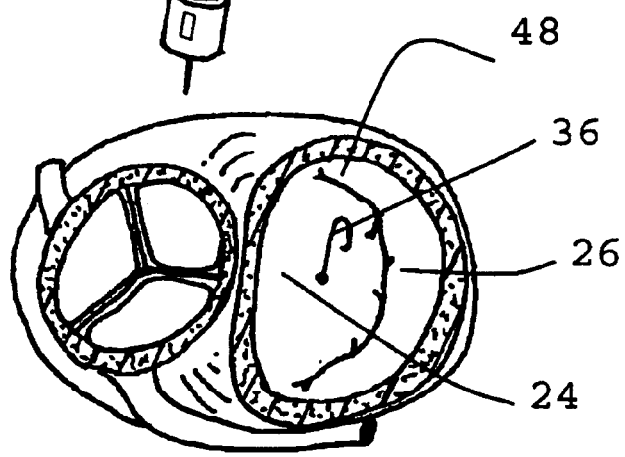
Fig. 10b

Fig. 10
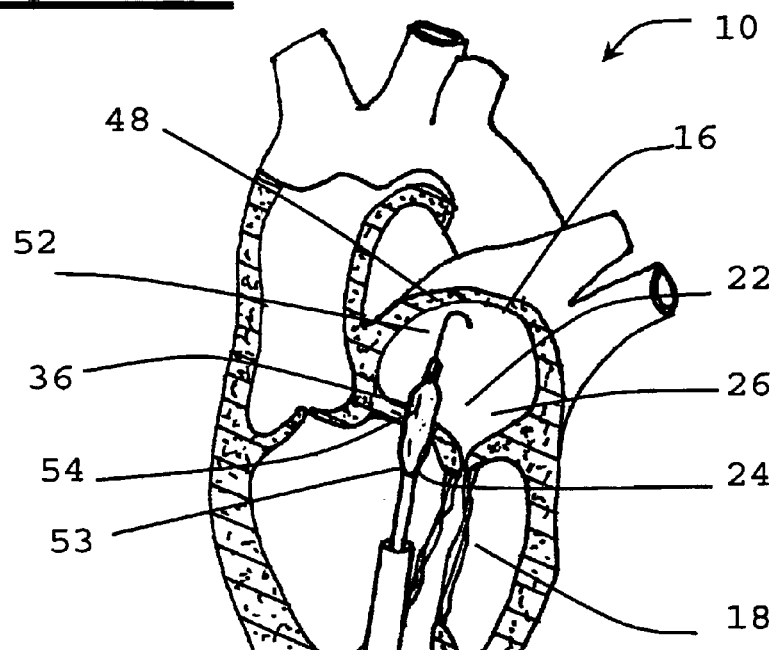
Fig. 10c
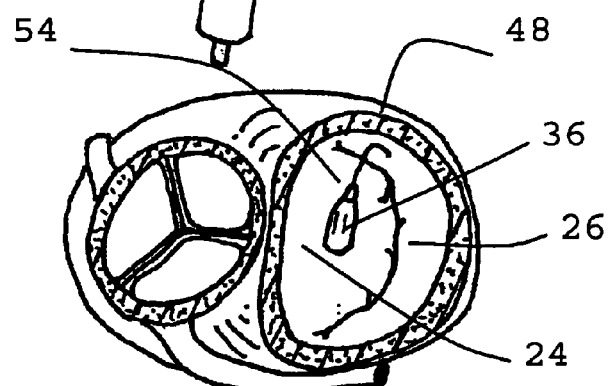
Fig. 10d

Fig. 10
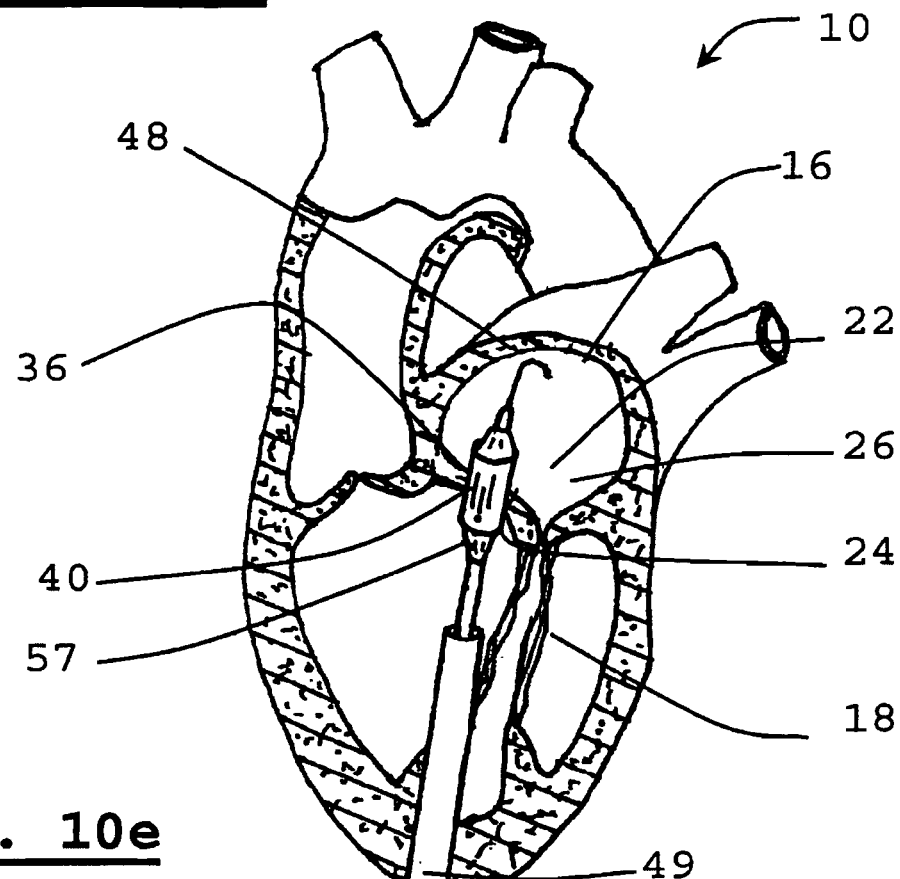
Fig. 10e
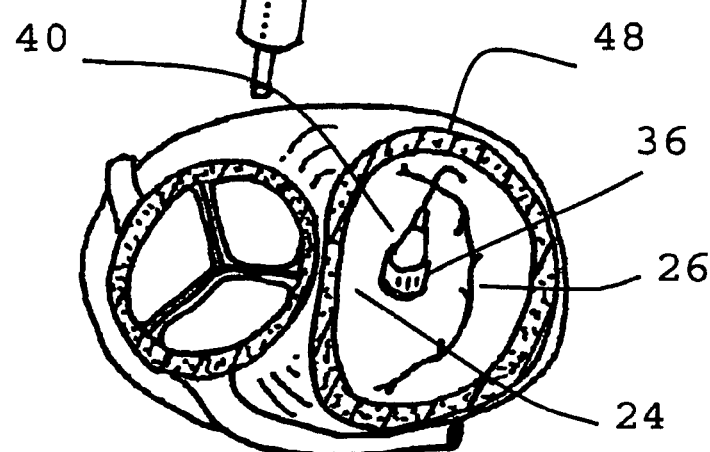
Fig. 10f

Fig. 10
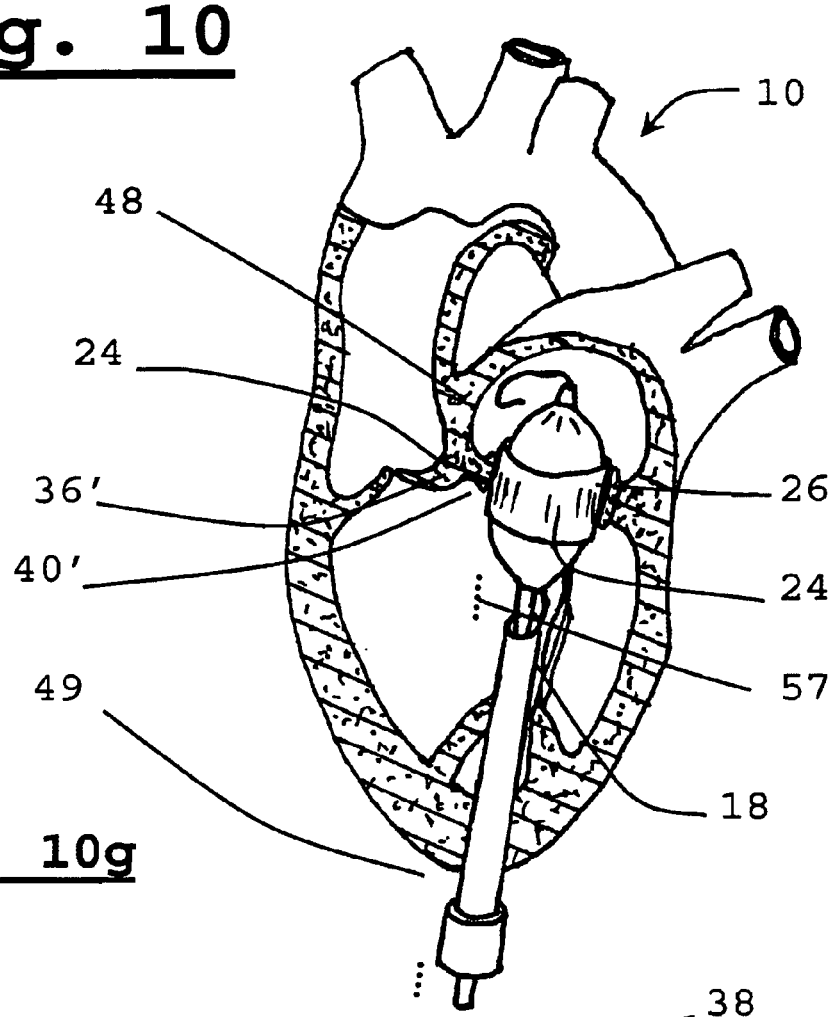
Fig. 10g
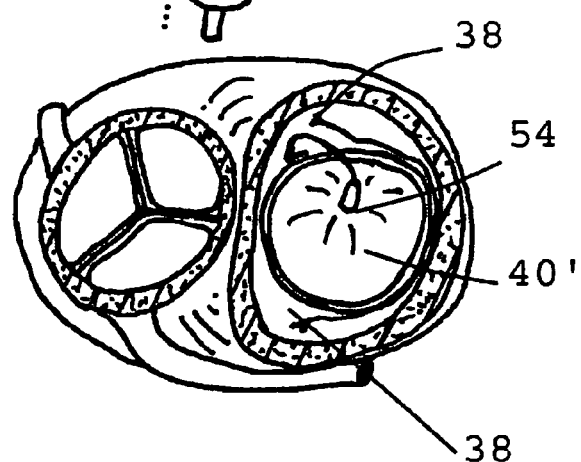
Fig. 10h

Fig. 10
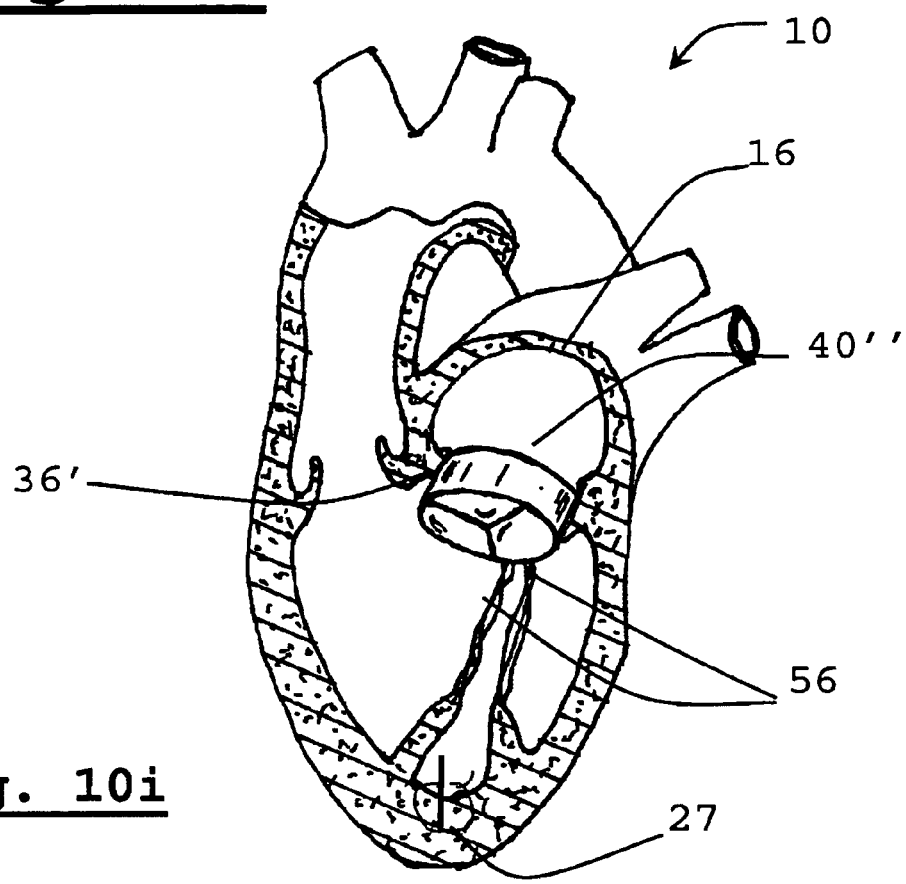
Fig. 10i
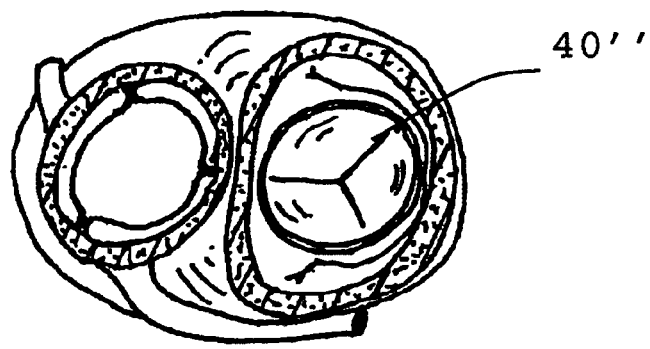
Fig. 10j

Fig. 11
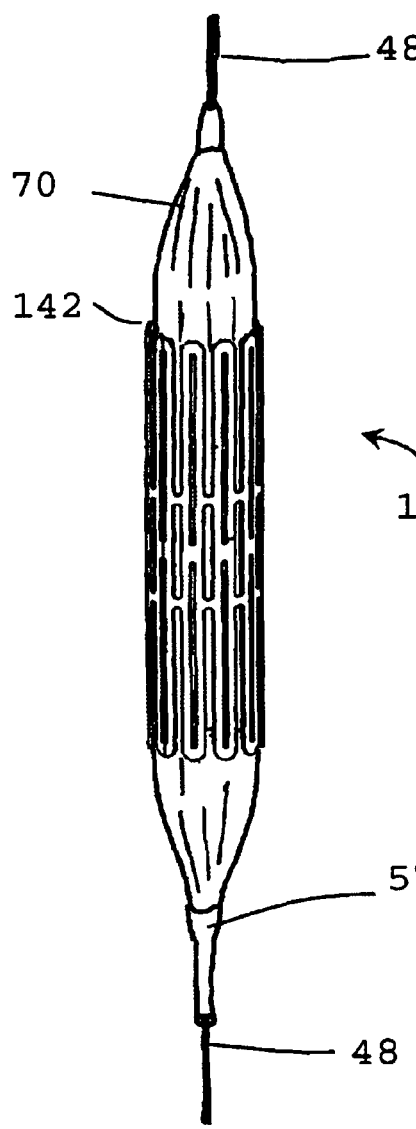
Fig 11a
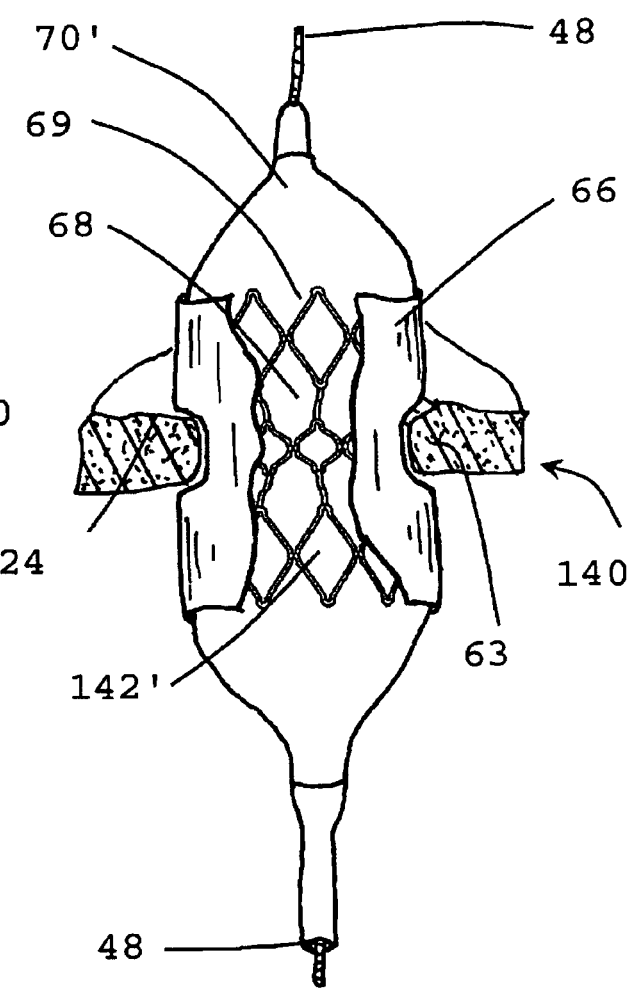
Fig 11b

METHOD FOR IMPLANTING PROSTHETIC VALVE

FIELD OF THE INVENTION

The present invention relates to methods and devices for treating dysfunctional mitral valves, particularly to new medical procedures for installing a prosthetic valve in a new location.

BACKGROUND OF THE INVENTION

Atrioventricular (AV) valves are cardiac valves that prevent backflow from the ventricles into the atria during systole. They are anchored to the wall of the heart at the fibrous skeleton by anchoring tendons named chordae tendineae. The chordae tendineae are attached to papillary muscles. Together, the papillary muscles and the chordae tendineae keep the valves from prolapsing into the atria when they close during systole. The actual opening and closing of the valves is caused by the pressure gradient across the valve. The left side AV valve is a bicuspid valve having two flaps or leaflets, and is commonly known as the mitral valve due to its shape being reminiscent of a bishop's mitre. The right side AV valve is a tricuspid valve, having three flaps or leaflets. Both of these valves may be damaged and dysfunctional, resulting in leakage during systole, requiring the valves to be repaired or replaced.

While the mitral valve is generally an ellipse or D-shaped, the tricuspid valve is more circular. The left ventricle pumps oxygenated blood around the body and so the mitral valve has to withstand a much higher pressure than the tricuspid valve which only has to pump deoxygenated blood to the nearby lungs. Mitral valve regurgitation causes heart murmurs and may have severe physiological consequences.

Occasionally, the mitral valve is congenitally abnormal or destroyed by infection or a bacterial endocarditis. More often the mitral valve becomes degenerative with age or as a result of rheumatic fever. There are different valvular heart disorders associated with the mitral valve such as mitral stenosis and mitral regurgitation, In the case of mitral stenosis, the valve orifice, i.e. the cross-section available for blood passage is reduced because of calcium nodes, leaflet thickening and/or reduced leaflet mobility, and, consequently, the valve does not allow normal blood flow. To overcome the damaged valve and too transport the same amount of blood, the left atrium requires a higher pressure than normal.

The constant pressure overload of the left atrium may cause it to increase in size and become more prone to develop atrial fibrillation and to lose the atrial kick. The loss of the atrial kick due to atrial fibrillation can cause a precipitous decrease in cardiac output. A reduction in cardiac output, associated with acceleration of heart rate and shortening of the diastolic time, frequently leads to congestive heart failure.

In most cases mitral stenosis is due to rheumatic heart disease. The treatment options for mitral stenosis include medical management, surgical repair, surgical replacement of the valve, and percutaneous balloon valvuloplasty.

Mitral regurgitation MR is caused either by ischemic heart disease (Ischemic MR) or mitral valve prolapse (also referred to as degenerative myxomotous)—(hereinafter MVP). Ischemic MR is a result of ventricular remodeling which is secondary to ischemic heart disease. The heart's posterior wall, which is not attached to the heart's fibrous skeleton, dilates. As a result of the change of the left ventricular geometry, the posterior leaflet, which is attached to the posterior heart wall, is displaced and misaligned from the anterior leaflet which results in mitral regurgitation.

MVP is a condition caused by degeneration of the valve's connective tissue. Patients with classic MVP have surplus connective tissue. This weakens the leaflets and adjacent tissue, resulting in increased leaflet area and elongation of the chordae tendineae. Elongation of the chordae tendineae often causes rupture. Tweaked leaflets may be displaced in some portion of one or both of the abnormally thickened mitral valve leaflets into the left atrium during systole. Advanced lesions lead to leaflet folding, inversion, and displacement toward the left atrium. The abnormal leaflet structure leads to incomplete closure of the mitral valve and MR.

In mitral regurgitation, the heart has to work harder by pumping not only the regular volume of blood, but also the extra volume of blood that is regurgitated back into the left atrium. The added workload creates an excessive strain on the left ventricle, which can lead to heart failure.

While patients with mild to moderate mitral regurgitation caused by MVP might experience no symptoms, increasing severity, even without symptoms, increases the load on the left ventricle. Over time this can result in ventricular dilatation and congestive heart failure.

Mitral valve disease is conventionally treated by open heart surgery; either by surgical repair usually with an annuloplasty ring or by surgical replacement with valve prosthesis. There are some advantages to repairing a mitral valve rather than replacing it, especially in mild cases and in asymptomatic patients of MVP. Some studies suggest a lower mortality at the time of operation, a significantly lower risk of stroke, a lower rate of infection and improved long-term survival with mitral valve repair.

In some cases, such as when the valve is too damaged, mitral valves may require replacement.

Charles Hufnagel, a professor of experimental surgery at Georgetown University, developed an artificial heart valve and performed the first artificial valve implantation surgery in a human patient. The valve was a methacrylate ball in a methacrylate aortic-sized tube which did not replace the leaky valve but acted as an auxiliary valve. The first replacement valve surgeries were performed in 1960 by two surgeons who developed their ball-in-cage designs independently. Dwight Harken developed a double-cage design in which the outer cage separates the valve struts from the aortic wall. At the University of Oregon, Albert Starr, working with electrical engineer Lowell Edwards, designed a silicone ball inside a cage made of stellite-21, an alloy of cobalt, molybdenum, chromium, and nickel. The Starr-Edwards heart valve is still in use today.

A percutaneous heart valve implantation method was later developed by Edwards Lifesciences PVT Ltd. and is described in U.S. Pat. No. 6,730,118, which is herein incorporated by reference in its entirety. The main idea behind this method is implantation inside the stenotic region of a calcified native valve without removing the native valve. This method stents the stenotic valve open and uses it as an attachment means.

There are two primary types of artificial mitral valves: (i) ceramic or mechanical valves and (ii) tissue or biological valves. The so-called mechanical valves are currently made entirely from metal and/or pyrolytic carbon and are long-lasting. Mechanical valves, although durable, require lifelong anticoagulation drugs. Currently available mechanical valves come in several different designs, including single and double flap valves, and are manufactured by well-known companies such as St. Jude®, Medtronic®, Sulzer®, and others. Polymer leaf type valves are not yet in use, but several companies are in the process of developing such products. A new type of prosthesis based on artificial polymer materials such as polyurethane, nylon and Dacron® are being considered.

Tissue-based valves do not require ongoing usage of anti anticoagulation drugs. However, they tend to degenerate over time and may require replacement within 10 to 15 years, necessitating a further operation. There is a wide range of biologically based replacement valves made of natural valves or composed of biological materials. The membrane comprising the one way valve leaflets is traditionally made of a native heart valve or pericardium harvested from different species, such as bovine, equine and porcine. These are assembled and marketed by well-known companies such as Edwards Lifesciences®, Medtronic®, Sulzer®, Sorin®, and others.

Mitral valve replacement may be performed robotically or manually. Surgical valve replacement or repair is often a demanding operation as it requires cardiopulmonary bypass and it can expose patients, especially elderly ones, to many risks.

A large variety of percutaneous or transcutaneous medical procedures are currently being developed and practiced. For example, transcatheter procedures are known for replacement of aortic and pulmonary heart valves. These procedures, which are performed under local anesthesia in the cardiac catheterization lab, rather than by cardiac surgery, offer tremendous benefits to these patients. According to such approaches, the valve is inserted on a delivery device similar to a catheter or a sheath and then implanted in the desired location via access through a large blood vessel such as the femoral artery, for example. It involves making a very small perforation in the patient's skin such as in the groin area to access the femoral artery. This minimally invasive option is usually safer than open heart surgery, and recovery times are typically shorter.

Minimal invasive transcatheter Mitral repair procedure may be accessed using different approaches for instance transeptal or transfemoral or transapical approaches. In the transapical approach, a small surgical incision is made and a catheter or a sheath is inserted between the ribs and into the apex of the beating heart, and the valve is manipulated through the sheath or catheter into the implantation site. In the transfemoral approach, a sheath or a catheter is inserted through the femoral artery and the valve is advanced retrogradely through the sheath to the implantation site in the arterial side. In the transeptal approach, the right atrium is accessed via the vena cava which may be accessed through the subclavian vein. Then the left atrium is accessed by piercing the interatrial septum, perhaps using a mechanical or laser tool.

In transcatheter procedures, access to the native diseased valve is limited. Hence removal of the old valve is in many cases impossible and the prosthetic valve is implanted on top of or over the old valve, as described, for example, in U.S. Pat. No. 6,730,118, which is assigned to Edwards Lifesciences PVT Ltd.

To enable implantation of prosthetic replacement valves using a transcatheter approach, collapsible prosthetics have been developed. The folded or crimped profile of the prosthetic valve, directly influences the ability to insert the valve into the femoral artery or vein without causing trauma to the blood vessels whilst transporting the valve to the implantation site. Accordingly, a smaller profile allows for safer treatment of a wider population of patients.

The valve prosthesis remains folded or crimped until it reaches the proper location where it is expanded. Such crimping was once considered detrimental to leaflet structure, causing tears and calcification to leaflets; however these issues have largely been resolved. The transcatheter valve replacement approach is similar to the use of coronary stents that has been used successfully over the last few decades.

Typically the valve is constructed from a metallic frame, referred to as a stent, and a membrane constructed from a one-way valve mounted onto the stent.

The stent typically comprises a substantially cylindrical tube or mesh sleeve usually made from metal. The design of the stent material permits the stent to be radially crimped and expanded, while still providing sufficient rigidity such that the stent maintains its shape once it has been enlarged to a desired size.

Percutaneous heart valves are, similarly to stents, divided into two main types: self expandable valves and balloon expandable valves.

A shape memory alloy (SMA, smart metal, memory metal, memory alloy, muscle wire, smart alloy) is an alloy that "remembers" its original, set shape, and which returns to that shape after being deformed.

The three main types of shape memory alloys are the copper-zinc-aluminium-nickel, copper-aluminium-nickel, and nickel-titanium (NiTi) alloys also known as nitinol.

NiTi alloys are fully biocompatible and may be used in prosthetics and surgical procedures. They are, however, generally expensive. They change from austenite to martensite upon cooling. The transition from the martensite phase to the austenite phase is only dependent on temperature and stress, and, in contradistinction to most phase changes are time-independent, as there is no diffusion involved. It is the reversible diffusionless transition between the two phases that allow the special properties to arise. An additional material characteristic of these SMA materials is super-elasticity, self expandable valves are made of super elastic materials which may have an elastic allowable strain characteristic of around 8% as opposed to the typical elastic (i.e. reversible) strain of steels and stainless steels which is up to 1%. Valves fabricated from such shape-memory alloys may be compressed to a very small diameter which can be kept in the small configuration within a constraining tube, and, once released from the constraining tube, they expand to a final larger diameter. For example a crimped diameter of such a valve or stent may be 5 to 6 mm while the expanded diameter can be 24-32 mm. The environmental temperature influences the process of reducing and expanding the stent using the shape memory thermal characteristic.

Balloon expandable valves are constructed from metals that have plastic deformation properties such as stainless steel or cobalt chromium alloy. They can be transported to the implantation position in the small crimped diameter configuration and then radially expanded by inflating a balloon, thus opening the valve to its working configuration.

The membrane constructing the one way valve is traditionally made of pericardium harvested from different species, mainly bovine. However, they can be also made of artificial material such as polyurethane, nylon, Dacron or even a thin membrane of Nitinol. \The membrane may also be made of a harvested native valve such as a porcine aortic heart valve.

Another important concern of valve replacement is securing the prosthesis within its proper location. Typically, the primary attachment mechanism of the prosthetic valve to the native valve is friction, which is generated by radial contact forces between the stenotic valve and the frame of the valve. Thus proper sizing is an important factor for securing the attachment of the prosthetic valve to the native valve to provide good sealing, and, to avoid, for example, paravalvular leaks.

Structural and physical parameters assist the stable anchorage of a prosthetic valve over the native valve. For example, the prosthetic aortic valve is naturally located in a circular tubular blood vessel, the aorta, and is anchored to a strong fibrous construction around the whole circumference. Additionally in most cases the diseased native aortic valve is calcified and thus rigid, further assisting the stable anchoring of the prosthetic aortic valve. Replacement methods for aortic valves may be unsuitable for replacing mitral valves which differ therefrom, both anatomically and geometrically (morphologically). The mitral valve is ellipse shaped, non-tubular and has an uneven circumference. Its leaflets are inserted on the circumference of the mitral annulus. The inner, or anterior leaflet, is in continuity with the aortic annulus and the fibrous trigones and is made of a constructive fibrous tissue. However, the outer, posterior leaflet is continuous with the posterior ventricle wall, which can dilate in some cases since it is not connected to the cardiac skeleton. Positioning and expanding a transcutaneous circular prosthetic valve (e.g. transcutaneous prosthetic aortic valve) within the opening of the ellipse shaped diseased mitral valve may result in inadequate sealing of the mitral valvular annulus, thereby resulting in severe regurgitation. Furthermore, a circular valve deployed in a standard fashion will have poor anchoring and the valve is prone to detach and migrate from its position, to the detriment of the patient.

The valve leaflets are connected to the anterolateral and posteromedial papillary muscles by chordae tendineae. Primary chordae are attached to the free edge of the valve leaflet, and secondary chordae are attached to the ventricular surface of the leaflets. These chordae are important for the proper structure and function of the mitral valve and implanting a prosthetic replacement valve over the native mitral valve could potentially sever the chordae. If the chordae are severed, then the ventricular wall is no longer anchored to the valve apparatus and the tethering effect of the chordae is lost. As a result, left ventricular wall stress increases and left ventricular function deteriorates.

Several prosthetic valves are known. See for example WO 98/29057 and U.S. Pat. No. 5,411,552, U.S. Pat. No. 6,168,614 and U.S. Pat. No. 5,840,081. A method for deploying a prosthetic valve device in body ducts has been described in U.S. Pat. No. 7,510,575. An apparatus for replacing a diseased AV valve using a minimally invasive, percutaneous approach has been described in U.S. Pat. No. 7,611,534, where the apparatus has at least one anchoring portion which is anchored in an opening extending from the atrial chamber.

The main disadvantage of the methods for valve implantation described in the aforementioned patents is that they are not suitable for mitral valve replacement, mainly due to lack of or insufficient or cumbersome anchorage of the apparatus, and their application tends to risk continued regurgitation, i.e. blood backflow from left ventricle to left atrium upon systole. Furthermore, the prosthetic valve apparatus is inserted over the native valve and thus there is increased risk of rupturing chordae tendineae or damaging the healthy leaflet. Thus, there is a long-felt need for a method which provides proper anchorage for mitral valve prosthesis, securing it in its proper location after implantation without severing the chordae tendineae and which also prevents paravalvular regurgitation.

It is an object of the present invention, to provide a method for percutaneously implanting a prosthetic mitral valve apparatus to replace the function of a dysfunctional or diseased mitral valve without severing the chordae tendineae. It is a further object of the invention to provide a solution for paravalvular leakage and regurgitation.

SUMMARY OF THE INVENTION

The present invention relates generally to the field of medical procedures, and specifically to a method for the implantation of a prosthetic replacement valve apparatus in a novel and non obvious location in a patient's body which neutralized and replaces the function of a native dysfunctional mitral valve. The replacement causes the closing of the native valve and thus results in a solution for paravalvular leakage and regurgitation.

In an embodiment of the present invention, a method for treating a patient with a diseased or dysfunctional valve, specifically a diseased or dysfunctional mitral valve is described. The method comprises the steps of: piercing an aperture through a first leaflet of a valve; advancing and positioning a collapsed prosthetic valve apparatus comprising a one-way valve mounted on an expandable valve seating into the aperture; expanding the expandable valve seating and forcing an outer edge of the first leaflet against a second leaflet, thereby inhibiting the natural separating of the first and second leaflets in diastole by forcing the edges of the leaflets together and preventing their separation, the prosthetic valve providing an alternative passageway for blood pumped whilst inhibiting back-flow in systole. Typically the valve is a mitral valve.

Optionally, the piercing is by a mechanical tool. Alternatively, the piercing is by a laser tool. Alternatively again, there is no step of piercing and the prosthetic valve is inserted in a natural fissure or tear in the leaflet.

Typically, the first leaflet is an anterior leaflet of the mitral valve.

In one embodiment of the invention the first leaflet of the mitral valve is accessed via the left ventricle and access is by a transvascular approach route, optionally using transcatheterization. Optionally the piercing is performed when the heart is in systole, causing the anterior mitral valve leaflet to coapt with the posterior mitral leaflet.

In another embodiment of the invention, the left ventricle is accessed transapically and the piercing is performed when the heart is in systole, causing the anterior mitral valve leaflet to coapt with the posterior mitral leaflet.

In another embodiment of the invention the right atrium is accessed via the vena cava and the left atrium is accessed by piercing the septum interatrial.

In some embodiments of the invention, the expandable seating is an annular member and the step of expanding the expandable seating comprises inflating a balloon within the annular member.

In other embodiments, the expandable seating comprises a shape-memory super-elastic alloy that expands as it is released from its constraining tube and/or approaches body temperature. Optionally, the shape memory alloy is an alloy of nickel-titanium.

According to some embodiments of the invention, the valve is coated with a material which aids tissue growth.

In some embodiments, the expandable seating has a circumference having a textured surface which engages surrounding tissue to secure the valve apparatus in place.

In one embodiment of the invention, the expandable seating comprises self-expanding shoulders which assist in engaging surrounding leaflet tissue to secure the valve in position.

According to some embodiments of the invention, the method comprising a preliminary step of obtaining regulatory approval for the prosthetic valve for insertion into an aperture made within a leaflet of the valve.

According to some embodiments of the invention, the method comprises a preliminary step of packaging the prosthetic valve apparatus in a package labeled as appropriate for insertion into an aperture made within a leaflet of the valve.

According to some embodiments of the invention, the method provides a preliminary step of co-packaging the prosthetic valve apparatus together with instructions describing its suitability for insertion into an aperture made within a leaflet of the valve.

According to some embodiments of the invention, the method comprises a preliminary step of marketing the prosthetic valve apparatus for insertion into an aperture made within a leaflet of the valve.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2a and 2b are schematic top views of mitral valve leaflets, with prosthetic valve apparatus implanted in anterior leaflet in collapsed and expanded configuration;

FIGS. 10 a-j represent schematically, the steps of implanting and securing a mitral prosthetic valve apparatus within a novel location, which allows it to replace the functionality of a dysfunctional valve, according to an embodiment of the present invention;

FIGS. 11a and b depict a schematic view of a balloon expandable valve having an indented circumference and a textured surface which assists in securing the valve in its proper position, according to an embodiment of the present invention;

Figure 1:
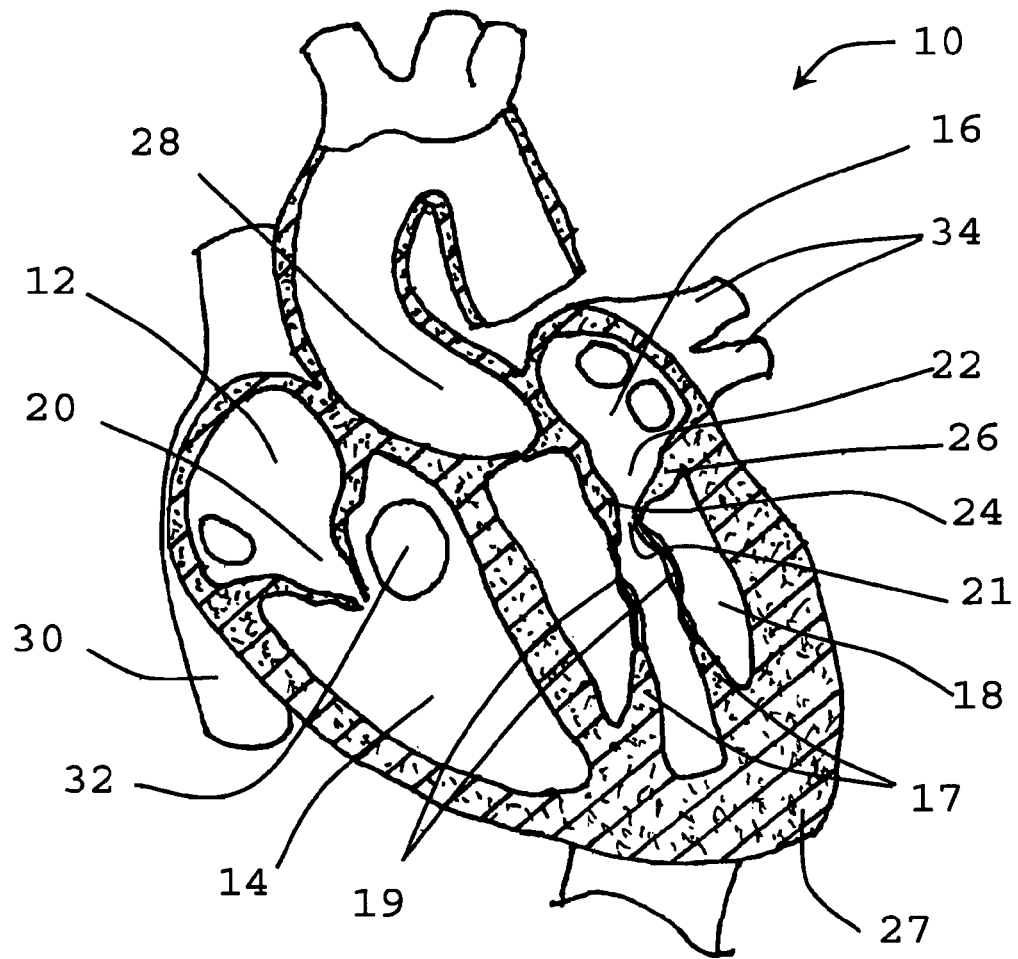
FIG. 1 is a vertical section through a heart.

For clarity, method steps are annotated with letters and the illustrative Figures with numbers. The same numbering scheme is used consistently where appropriate to aid clarity

DETAILED DESCRIPTION OF THE EMBODIMENTS

The present invention relates to a method for implanting a prosthetic valve apparatus in a novel and unexpected location. In this manner, the function of a prosthetic mitral valve is provided by the prosthetic valve and the native dysfunctional valve is voided, thereby avoiding paravalvular leakage. The method takes advantage of the special structural features of the tissue of the native leaflets and annulus of the mitral valve to keep the valve secured in place. The anterior leaflet extends across the annulus, which is an area of heart wall tissue at the junction of the atrial and ventricular walls that is relatively fibrous and significantly stronger than leaflet tissue. It provides structural support for the prosthetic valve and prevents its detachment from the novel orifice. It will be noted that the free edge of the valve leaflet has a reinforced, sinewy structure that is significantly stronger than central portions of the leaflet.

The approach of the invention is in contradistinction to previous approaches which typically deployed similar prosthetic valves in the native orifice of the valve, using the ducts for anchorage. For example in U.S. Pat. No. 7,611,534 to Kapadia, et al titled "Percutaneous atrioventricular valve and method of use", an anchoring portion of the apparatus is anchored in the pulmonary vein and the main body portion is deployed in the left atrium.

It is particularly noted that different known prosthetic valve apparatuses may be used with embodiments of the present invention. For example a particular valve prosthesis of the type depicted in U.S. Pat. No. 7,618,446 to Andersen et al. titled "Valve prosthesis for implantation in the body and a catheter for implanting such valve prosthesis" or that described in U.S. Pat. No. 7,611,534 to Kapadia, et al titled "Percutaneous atrioventricular valve and method of use" may be used with the presently disclosed method, rendering it more cost effective and easy to use.

It will be appreciated that implantation of a prior-artprosthetic in the manner intended by the manufacturers, i.e. in series with the natural valve, results in a given prosthetic being suitable for insertion in a very specific size and type of heart and requires the manufacturing of and availability of a whole selection of prosthetics to treat a population of patients. In contradistinction, in the new methodology described herein, the same prosthetic could be used for repairing a heart, irrespective of the size, age or gender of the patient. Hence this method enables enhanced tolerance to sizing as there is no need to specify a mitral valve that is accurately sized for the left atrium of a specific patient, and to create or select an appropriately-sized replacement apparatus. Essentially sizing need only take into account the functionality and proper blood flow, with the valve being big enough to enable proper sealing, but not being too big to risk aortic valve dysfunction. It will thus be appreciated that relatively few prosthetics having different sizes and shapes will be sufficient to treat the vast majority of cases.

With reference to FIG. 1a, a vertical section through a heart is shown. The heart 10 consists of a right atrium 12, a right ventricle 14, a left atrium 16 and a left ventricle 18. The right and left atria 12, 16 are separated by the septum interatrial 15 (shown in FIG. 8). The right atrium 12 and right ventricle 14 are separated by a tricuspid valve 20, and the left atrium 16 and left ventricle 18 are separated by a bicuspid valve, also known as the mitral valve 22 that consists of an anterior leaflet 24 and a posterior leaflet 26 having edges that separate and come together as the left ventricle 18 dilates and contracts to force blood into the aorta 28. Deoxygenated blood from the body flows through the vena cava 30 into the right atrium 12 and is sucked into the right ventricle 14 through the tricuspid valve 20 as it dilates. The right ventricle 14 pumps the blood via the pulmonary artery 32 to the lungs. Oxygenated blood from the lungs flows via the pulmonary veins 34 into the left atrium 16 and is sucked into the left ventricle 18 via the orifice between the edges of the leaflets 24, 26 of the mitral valve 22. Systole of the heart 10 pumps the oxygenated blood through the aorta 28 and around the body. The anterior and posterior leaflets 24, 26 of the mitral valve 22 flex together as the left ventricle 18 contracts, to prevent blood being pushed back to the left atrium 16. Papillary muscles 17, chordae tendineae 19 and the heart apex 27 are also shown. The mitral valve 22 undergoes tremendous strain and the present invention is directed to novel methods of treating a patient with a dysfunctional or diseased mitral valve 22.

Prior art surgical treatment of dysfunctional mitral valves 22 involves either repairing the valve 22, and/or adding a prosthetic one-way valve in series with the mitral valve 22 to perform the same functionality, or inserting a prosthetic one-way valve between the leaflets 24, 26 of the native orifice 21 of the mitral valve 22. With reference to FIG. 2a, in contradistinction to the prior techniques, in the present invention, the dysfunctional or diseased mitral valve 22 is intentionally changed by creating a hole 36 in one of the leaflets 24, 26, inserting a prosthetic valve 40 in a collapsed state, and expanding the prosthetic valve to its expanded state 40', thereby wedging it into the hole 36, and widening the hole 36 into an orifice 36'. This novel approach of creating an additional orifice 36' and voiding the existing orifice 21 is counterintuitive and teaches away from the prior art. The method is advantageous since it avoids damaging chordea tindineae 19 and papillary muscles 17.

Thus with reference to FIG. 2a, a hole 36 is created in the mitral valve 22 by piercing the anterior mitral leaflet 24 away from the mating edges 38 of the leaflets 24, 26 and preferably near the center of the anterior leaflet 24. An expandable prosthetic valve 40 is introduced into the hole 36 in its collapsed state as shown in FIG. 2a and expanded therein to assume an expanded configuration 40' shown in FIG. 2b, wedging the expandable seating 42 of the prosthetic 40' into the hole 36, now an orifice 36', and forcing the edges 38 of the leaflets 24, 26 together, thereby closing and voiding the native orifice 21 of the valve 22.

Figure 3:
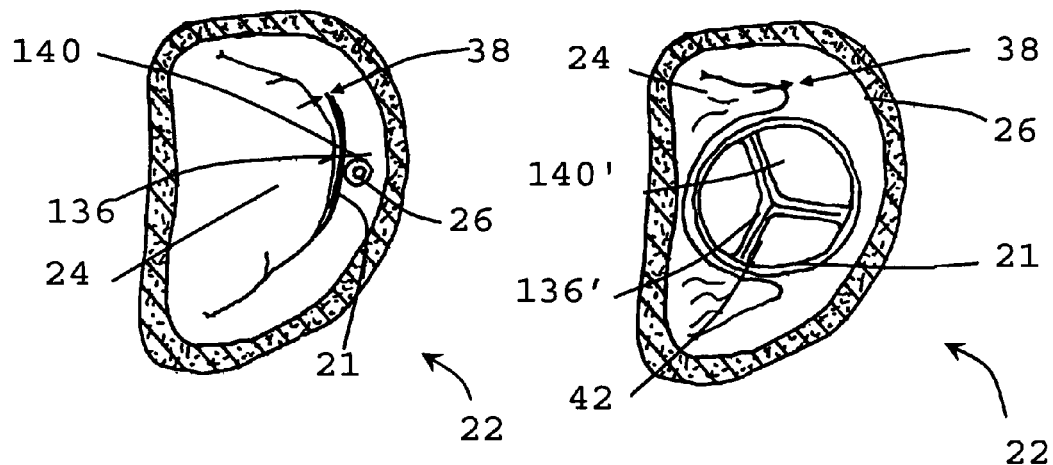
FIGS. 3a and 3b are schematic top views of mitral valve leaflets, with prosthetic valve apparatus implanted in posterior leaflet in collapsed and expanded configuration, respectively.

With reference to FIGS. 3a and 3b, in cases where the condition of the patient does not enable piercing of the anterior leaflet 24 or in different anatomical conditions where the shape of the leaflets 24, 26 and/or the native orifice 21 is in a different orientation to the normal state it is also possible to make the hole 136 in the posterior leaflet 26, to insert a prosthetic 140 whilst in its collapsed state, and to expand it into an expanded state 140' in situ, widening the hole 136 into an aperture 136', mutatis mutandis. Similarly, where a hole or tear pre-exists in one of the leaflets 24, 26 for whatever reason, the prosthetic 40 (140) may be inserted thereinto. The hole 36 (136) perforates all layers of the leaflet. i.e. the atrialis, fibrosa and spongiosa. Piercing is preferably performed when the heart 10 is in systole causing the edges 38 of the anterior and posterior mitral valve leaflets 24, 26 to coapt. It will be noted that the internal structure of the leaflets 26, 24 towards their edges 38 is fibrous and tough and the present invention avoids damaging this structure.

This new surgical procedure of installing a stent within a leaflet of a mitral valve provides a solution to a number of cardiac problems relating to the mitral valve 22 such as leaflet displacement, regurgitation and dilation. It will be noted that there is generally no need for positioning an annuloplasty ring, or for prior sizing. This method is thus both cost-effective and is suitable for a wide population. It also avoids rupture of the chordae tendeae (19 in FIG. 1).

Figure 4:
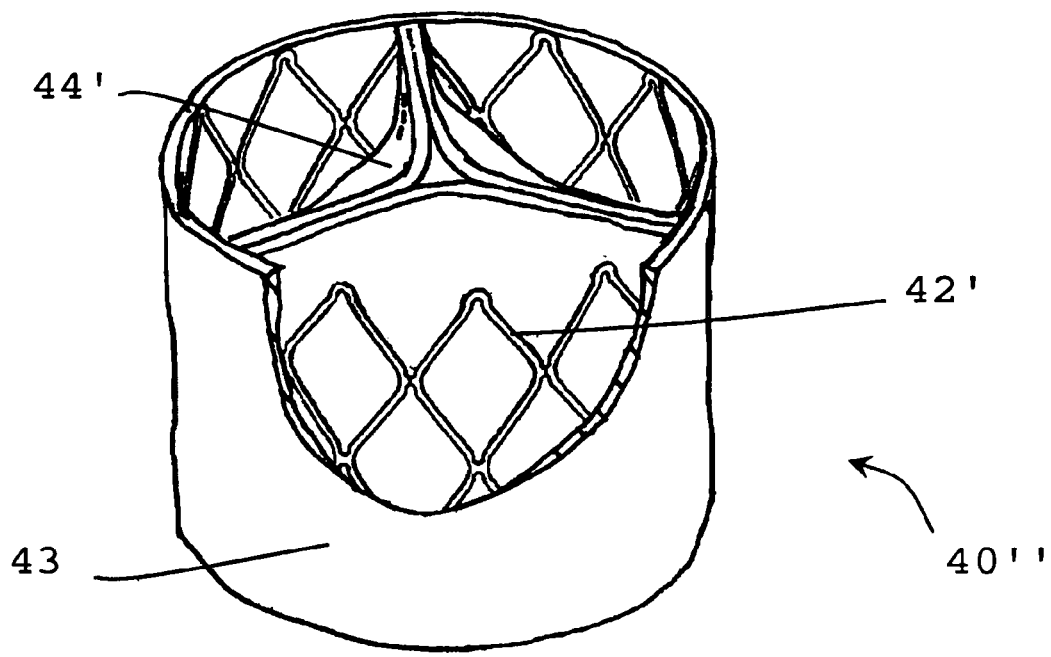
FIG. 4 shows a generalized prosthetic valve.

With reference to FIG. 4, a generalized prosthetic valve 40" is shown. Prosthetic valve 40" consists of an expandable valve seating 42' coupled to a one-way valve 44'. The expandable valve seating 42' may be covered with a fabric cover 43 which serves to prevent paravalvular leak and aids tissue growth.

It will be appreciated that the novel approach presented herein may be used with a range of expandable prosthetic valves, including valves that are currently available but were designed for insertion into the opening between the leaflets 24, 26 of the natural mitral valve 22.

Figure 5:
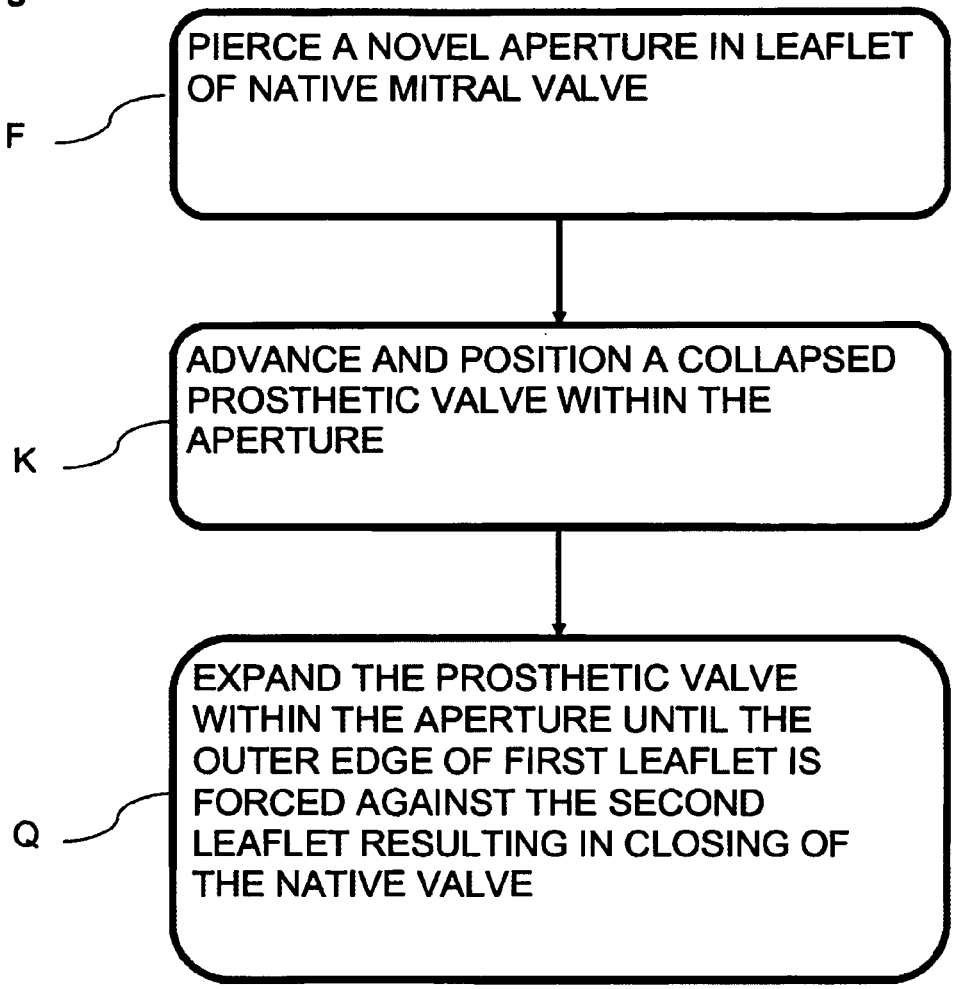
FIG. 5 is a flow chart describing generically, the essential steps of the method of the invention.

With reference to FIG. 5, a flowchart illustrating the main stages of a method for implanting a prosthetic valve 40 in accordance with the invention is shown. Firstly, a hole 36 is created in a leaflet 24 (26) of the native mitral valve 22—Step F. The piercing of the hole 36 may be performed with a mechanical tool such as a needle, hot wire or guide-wire. Alternatively a laser tool may be used. Various access routes including transvascular and transapical approaches are described below in FIGS. 6-8. The expandable seating 42 of a prosthetic valve 40 is positioned in the hole 36—Step K, and the expandable seating 42 is expanded—Step Q thereby opening the hole 36 into an aperture 36' and wedgingly locking the seating 42 within the aperture 36'. The expansion may be effected using an expansion arrangement comprising a balloon 70—(FIG. 11) inserted to the valve site via an introducing sheath 49 (FIG. 6) or catheter 50 (FIG. 7), or the valve seating 42 itself can be self-expanding, perhaps being fabricated from a shape memory alloy that may be introduced at a low temperature, and which undergoes a phase transformation as it warms to body temperature. The prosthetic valve may be alternatively fabricated from super-elastic material, so that is it is inserted into the hole 36 whilst constrained in an over-tube 60 (FIG. 12), and then expanded to a larger working diameter when released from the over-tube 60. As the valve 40 expands, it widens the hole 36 into an aperture 36' and forces the outer edge of the first, pierced leaflet against the second leaflet, thereby cancelling or at least minimizing the natural orifice 21 and closing of the leaflets 24, 26 by forcing the edges 38 (FIG. 2, FIG. 3) of the leaflets 24, 26 together and preventing their separation. Whilst voiding the native mitral valve 22, the prosthetic valve 40' wedged into the aperture 36 provides an alternative passageway for blood pumped from the left atrium 16 to the left ventricle 18 on dilation of the left ventricle 18 whilst inhibiting back-flow in systole and the expanded prosthetic valve 40' becomes operational so that the patient has cardiac output.

Figure 6:
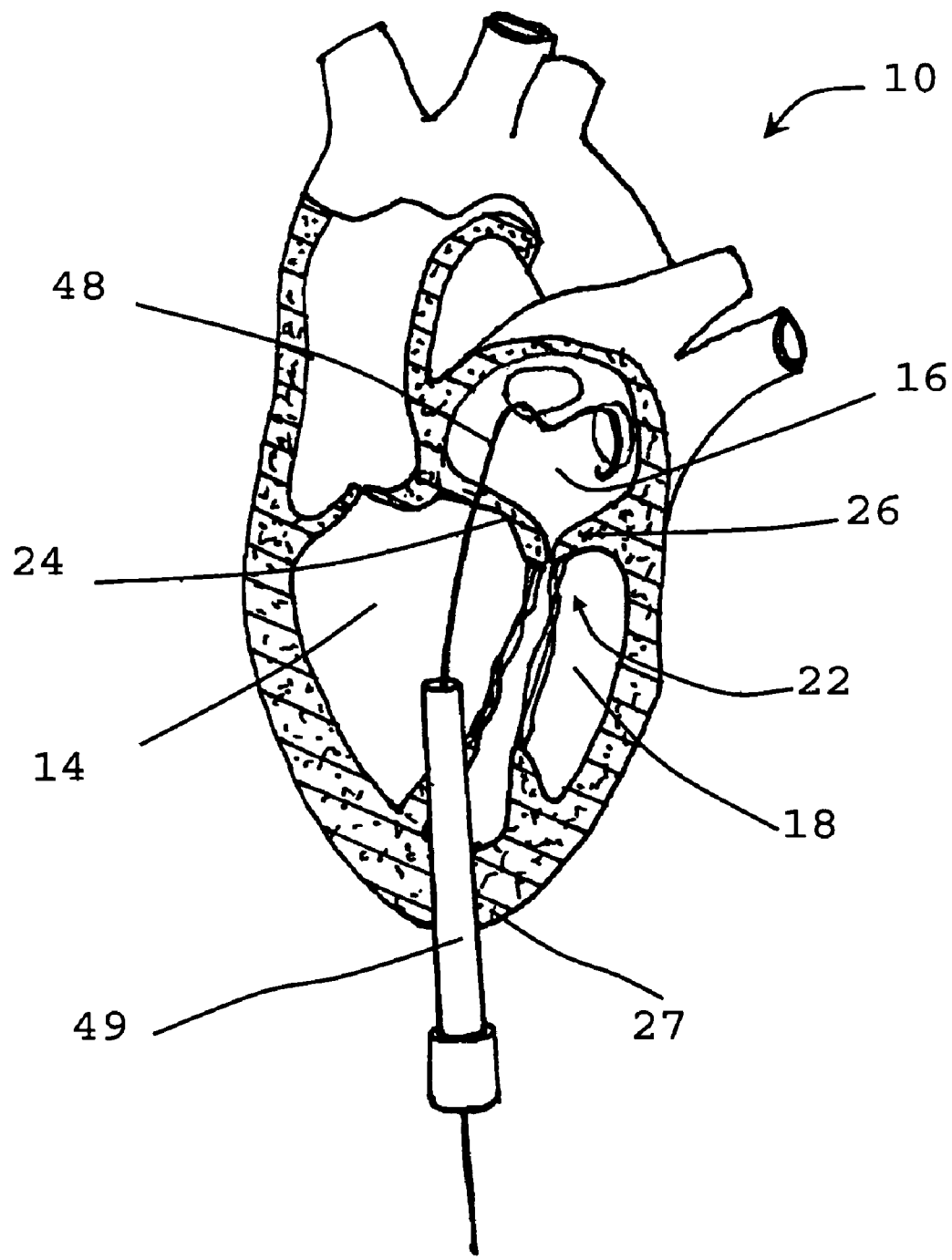
FIG. 6 represents schematically a transapical approach to implant heart valves, according to one embodiment of the present invention.

Access to the mitral valve 22 may be via the left atrium 16 or via the left ventricle 18, and there are a number of possible percutaneous routes. With reference to FIG. 6, access to the valve 22 may be transapically i.e. via the heart apex 27, typically piercing the anterior leaflet 24 when the heart 10 is in systole causing the anterior mitral valve leaflet 24 to coapt with the posterior mitral leaflet 26. Alternatively, as shown in FIGS. 7 and 8, access via the left ventricle 18 may be by a transvascular approach route, typically using transcatheterization.

Figure 7:
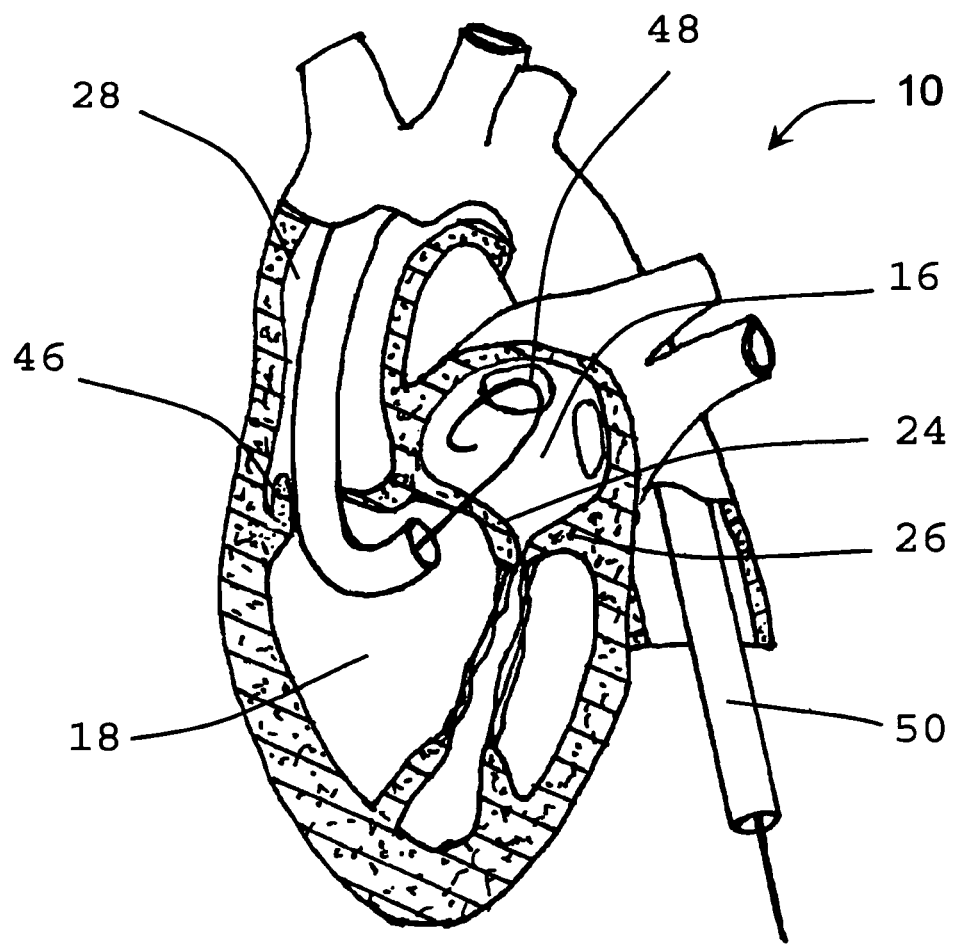
FIGS. 7 and 8 represent schematically different possible transcatheter approaches to implant heart valves, according to other embodiments of the present invention.

In FIG. 7, in a variant method, access to the anterior mitral valve leaflet 24 is via the left ventricle 18 with access to the ventricle 18 via the aorta 28 and aortic valve 46. Preferably the piercing is performed when the heart 10 is in systole causing the anterior mitral valve leaflet 24 to coapt with the posterior mitral leaflet 26.

Figure 8:
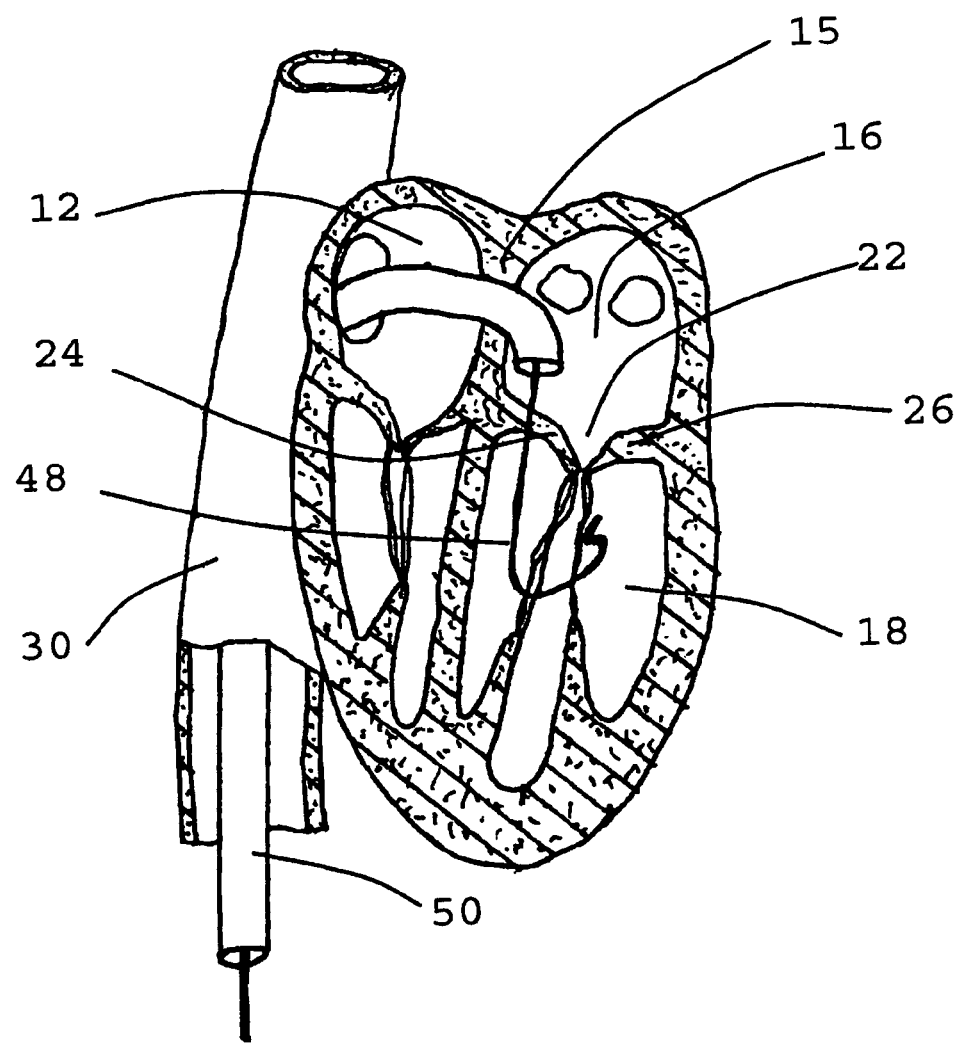

Alternatively, as shown in FIG. 8, the anterior leaflet 24 of the mitral valve 22 is accessed via the right atrium 12 by a transvascular approach, typically using transcatheterization, with the right atrium 12 being accessed via the vena cava 30 and the left atrium 16 is accessed by piercing septum interatrial 15.

It will however be appreciated that this novel positioning and usage of a prosthetic valve 40 may be by open heart surgery.

Figure 9:
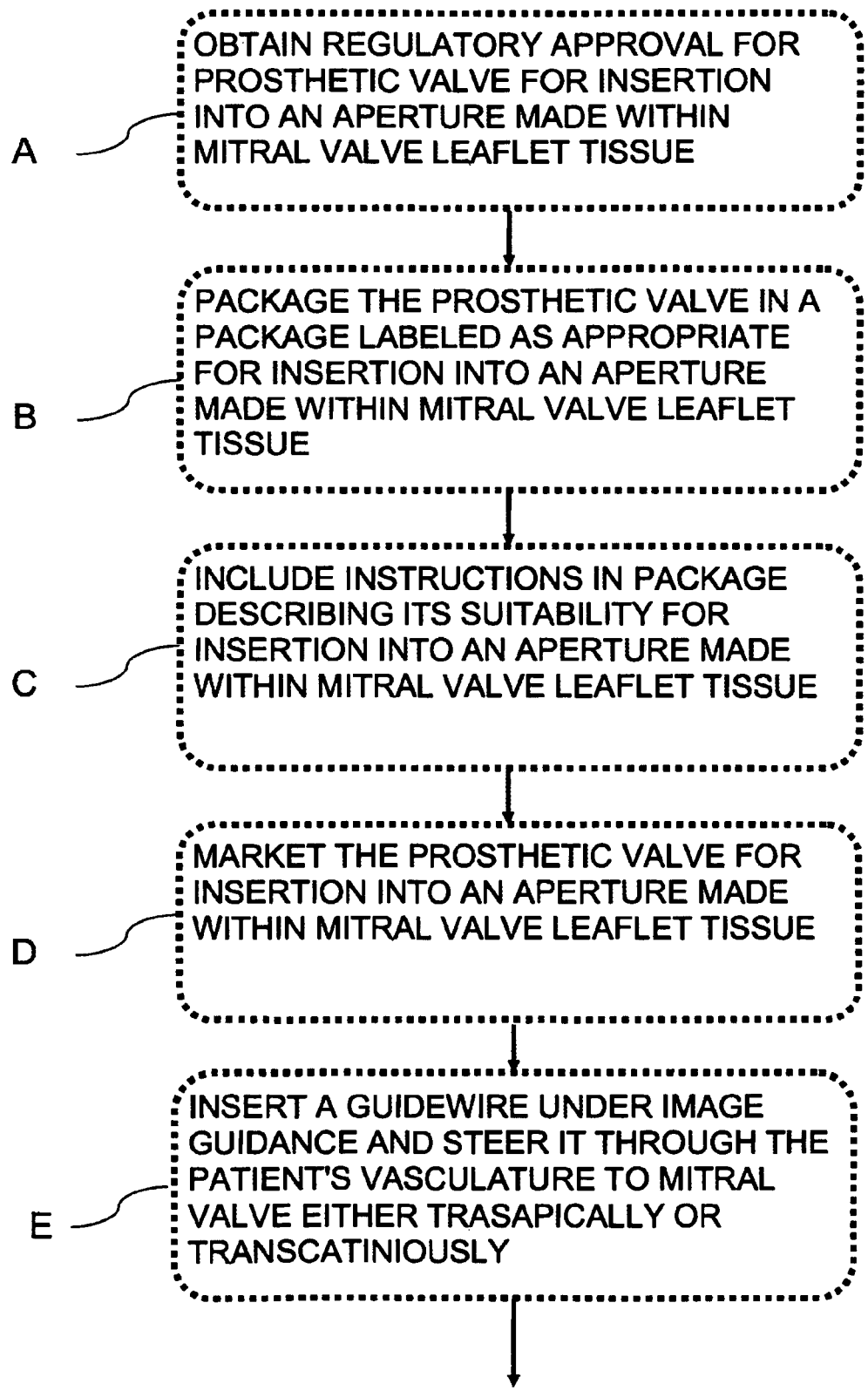
FIG. 9 is a flow chart showing the steps of implanting and securing a mitral prosthetic valve apparatus within a novel location, which allows it to replace the functionality of a dysfunctional valve, according to a detailed embodiment of the present invention.
Figure 9:
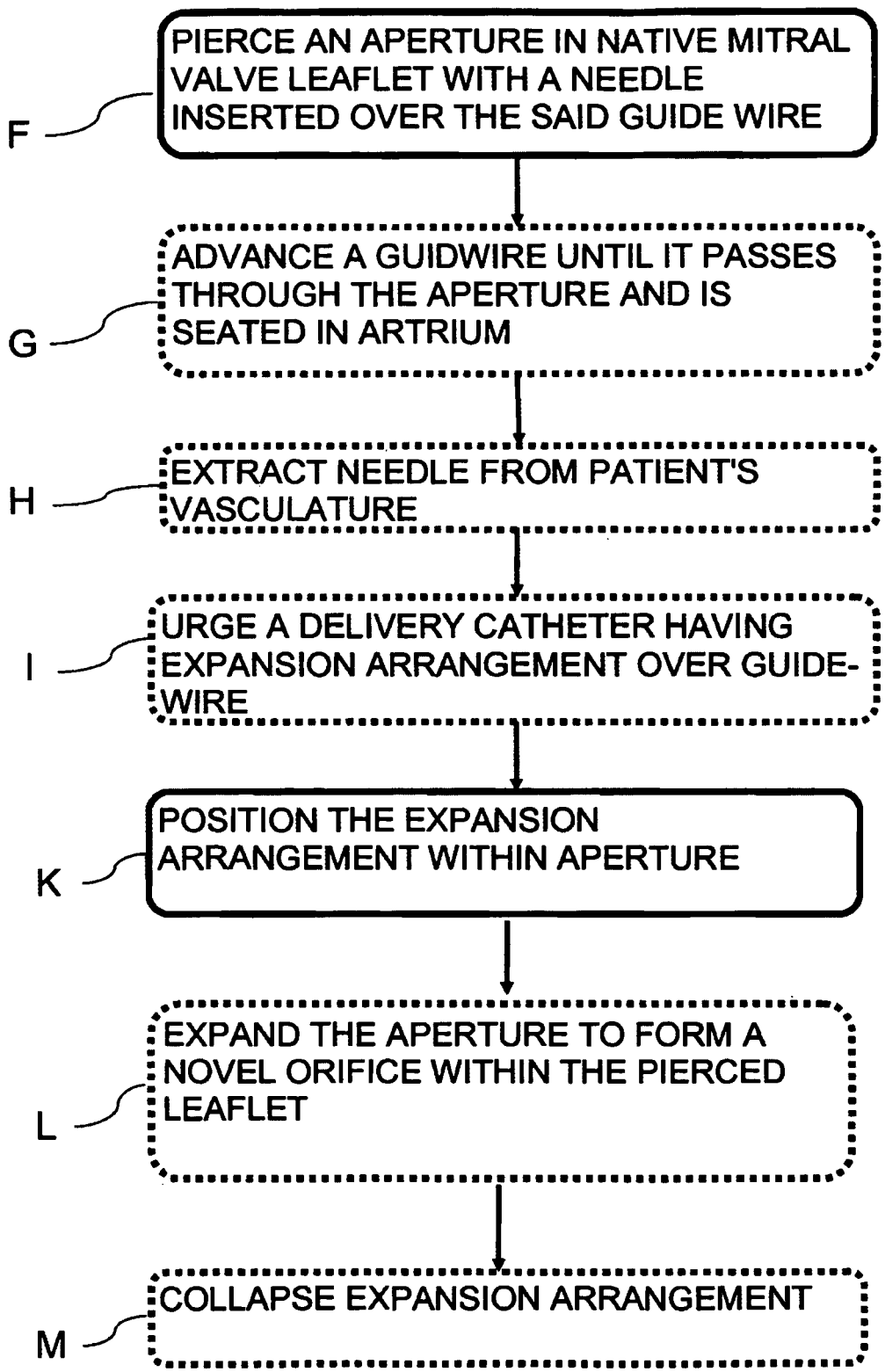
Figure 9:
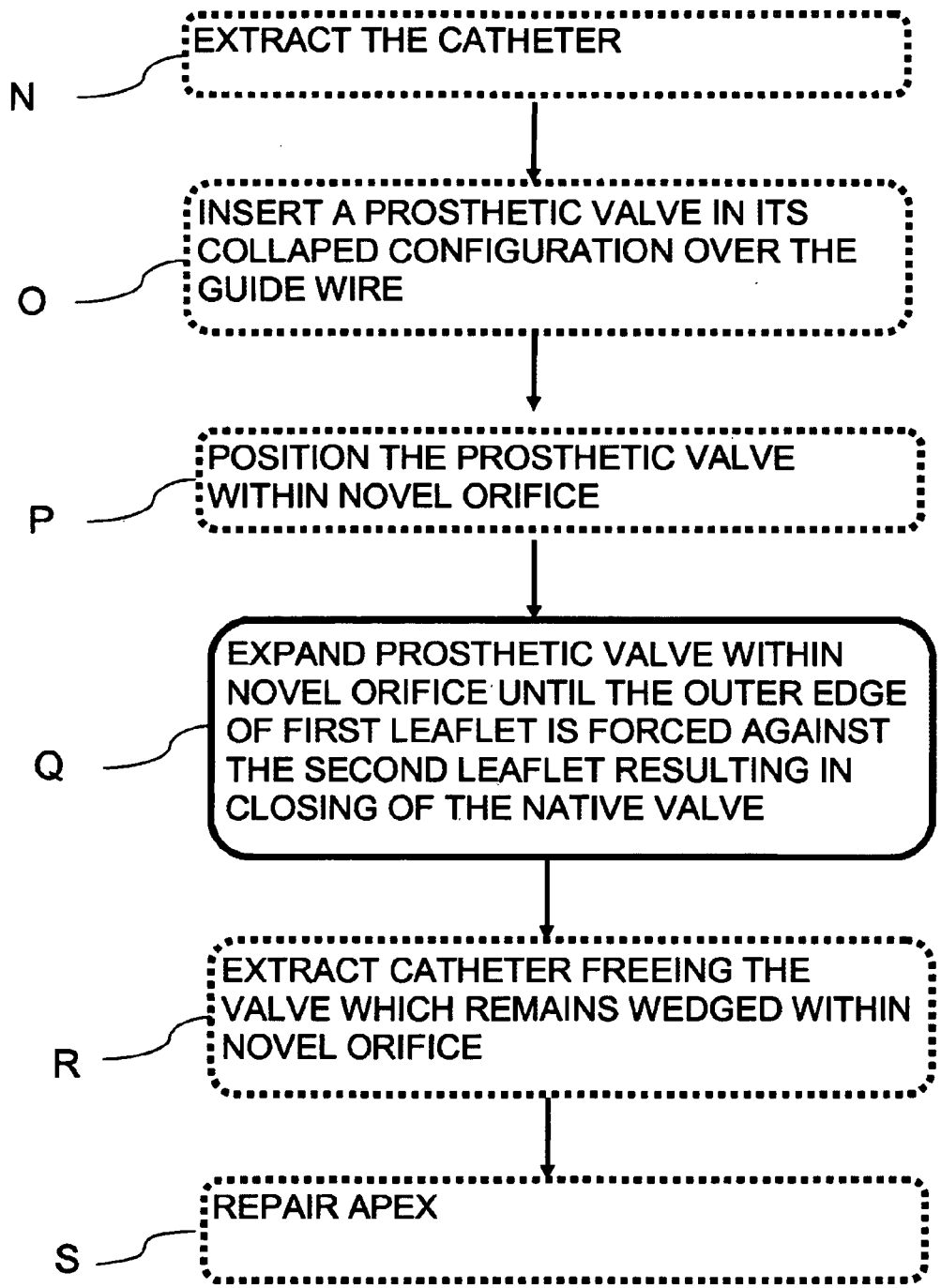

With reference to FIG. 9, by way of best mode enablement, a more detailed process is provided. Preferably one or more preliminary steps are performed prior to surgery. These may include obtaining regulatory approval for a new, variant of pre-existing prosthetic valve 40 for use with the methodology described hereinabove—Step A. Another useful preliminary step is to package the prosthetic valve 40 in a package (not shown) labeled as appropriate for insertion into an aperture or hole 36 made within the tissue of a leaflet 24 (26) of a mitral valve 22—Step B, and/or including instructions (not shown) for the novel operation as described herein within the package of the prosthetic valve 40—step C. Another preliminary step is marketing the prosthetic valve 40 for insertion into an aperture 36 made within the tissue of a leaflet 24 (26) of a mitral valve 22—Step D.

Thus (unless, open heart surgery is used), a mechanical tool such as a needle 39 (FIG. 10*a*) is typically inserted under image guidance and steered through the patient's vasculature either transapically via a sheath 49 (FIG. 10*a*) or transcatiniously via guiding catheter 50 (FIGS. 7 and 8) to mitral valve 22—step E. A first leaflet 24 (or 26) is pierced, at or near its center—step F, typically using a needle a guide wire, a laser tool, or perhaps a mechanical tool such as a scalpel or hot wire, to create a novel hole or aperture 36 (FIG. 10*a*). This may be performed when the leaflet is stretched during systole or the rim of the leaflet to be pierced being held with a tool such as a forceps or suture holder. Next a guide-wire 48 (FIG. 10*a*) may be advanced in the same manner until it passes through the aperture 36 (FIG. 10*a*), into the left atrium 16—step G and the needle, etc. 39 (FIG. 10*a*) is extracted from patient's vasculature—step H. Such a guide-wire 48 (FIG. 10*a*) will usefully have a very soft distal tip to protect the left atrium 16 which has a very delicate and thin myocardium.

A catheter, having an expansion arrangement, typically a balloon catheter 53 (FIG. 10*c*) I then urged through the sheath 49 and over the guide wire 48—step I. the expansion arrangement, in this figure, 10*c* an inflatable balloon 54 at the distal end of the catheter 53 is positioned in the aperture 36—Step K, aperture can be expanded—Step L to form a novel orifice 36' within the pierced anterior leaflet 24 (FIGS. 10*c*, 10*d*), possibly by inflating a balloon 54 (FIGS. 10*c* 10*d*). Next, the expansion arrangement of the catheter is collapsed—Step M, possibly by deflating the balloon 54 (FIG. 10*c*) and the catheter 53 (FIG. 10*c*) is extracted—Step N.

Then the prosthetic valve apparatus 40 (FIG. 10*e*), in its collapsed configuration, mounted on a delivery catheter 57, is tracked over the guide wire 48, to the implantation position in the novel orifice 36, the prosthetic valve being a self expandable valve or a balloon expandable valve as shown in FIGS. 10*e* and 10*f*—step O. Once the valve 40 is positioned within the novel orifice 36', it is expanded—Step Q. The expanded prosthetic valve 40' (FIG. 10*g*) forces the outer edge of the anterior leaflet 24 (FIGS. 10*g, h*) against the posterior leaflet 26 (FIGS. 10*g,h*), thereby cancelling or minimizing natural opening and closing of the mating edges 38 (FIG. 10*h*) of leaflets. The prosthetic valve 40' (FIGS. 10*g, h*) provides an alternative channel and valve for allowing blood to be pumped from left atrium 16 (FIG. 1) to left ventricle 18 (FIG. 1) on diastole and inhibiting back-flow therebetween in systole. Next the catheter 57 is extracted—step R, freeing the prosthetic apparatus 40'' (FIG. 10*i, j*), which remains securely wedged in the novel orifice 36' (FIGS. 10*i*, 10*j*) It will be noted that as the chordae tendineae 56 (FIG. 10*i*) are not severed, they continue supporting the left ventricle 18 (FIG. 10*i*), and the prosthetic valve 40'' (FIG. 10*i*) functions in place of the native valve 22 (FIG. 1). The apex 27 of the heart (FIG. 10*i*) may then be repaired—step S.

With reference to FIG. 11*a*, the use of a non-self-expandable valve apparatus 140 may be affected by compression of the valve seating 142 of the prosthetic valve apparatus 140 around an expansion arrangement such as a balloon catheter 57—seen here over a guide wire 48. Usefully the balloon 70 can be inflated by using a liquid that contains a contrast dye so that the shape and position of the balloon 70' (FIG. 11*b*) and valve apparatus 140 may be monitored during implantation using fluoroscopy, for example. With reference to FIG. 11*b* as stated previously, preferably the expandable seating 142' is covered with a fabric 66 that promotes tissue growth (fabric 66 is not seen in FIG. 11*a* for clarity purposes). A special design of the seating can be seen in FIG. 11*b*, by cutting the seating with non equal spacing 68 and 69 a shoulder, or dent 63 is created improving the hold and mounting of the valve 140 on the expansion site tissue, in this case the anterior leaflet 24.

With reference to FIGS. 12*a*, 12*b* and 12*c* when using a self-expandable valve seating 242, a catheter with an expansion arrangement is not required. In such instances the valve seating 242 is provided in its collapsed state 242*a* (FIG. 12*a*) and may be inserted within an over tube 60, typically made from plastic or metal, from which the valve 245 is ejected on implantation. Where the self-expandable seating 242 is fabricated from a shape memory metal, it may be configured into its collapsed state by cooling, by immersion in ice water, for example, and/or radially forced to its collapsed state by a crimping tool.

Figure 12:
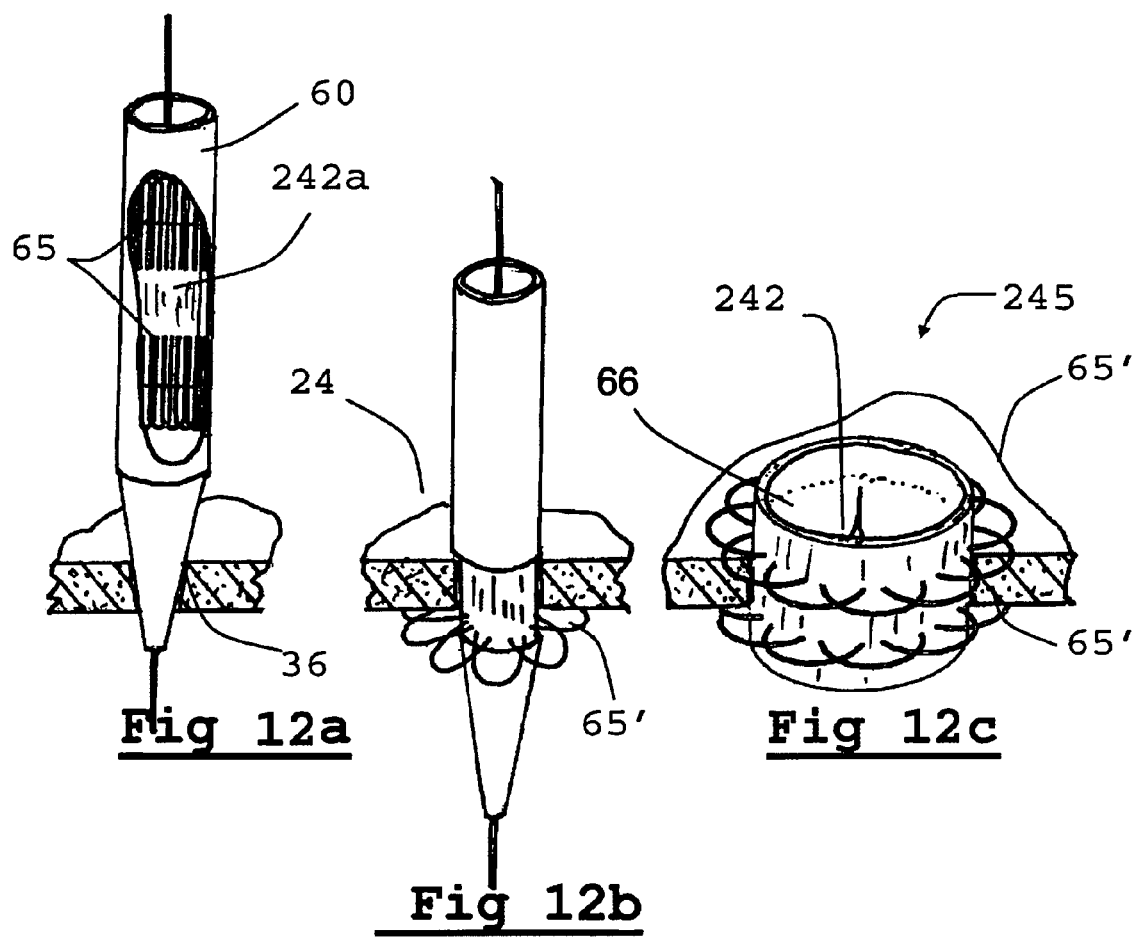
FIGS. 12a-c depict a perspective view of a self expandable valve with self expandable shoulders which assist in securing the valve in its proper position, according to another embodiment of the present invention.

The primary attachment mechanism of the prosthetic valve 245 to the tissue in circumference of the novel orifice 36' is friction. This friction is generated by radial contact forces between the tissue of the orifice 36' and the frame of the valve seating 242 of the prosthetic valve 245. This is typically aided and abetted by fabric cover 66 and the expandable valve seating 242 may further comprise different embodiments such as attachment means for affixing the expandable valve seating 242 to the novel orifice 36'. For example, according to one embodiment of the invention as shown in FIG. 12, the attachment means include a plurality of self expandable barbs 65 which are held in the crimped configuration by the over tube 60 (FIG. 12*a*), after the over tube is inserted through the valve leaflet 24 (FIG. 12*b*), it is pulled back exposing the first row of barbs 65' and allowing them to expand and create a shoulder which helps anchoring the valve 245 in its position within the orifice 36', thereby affixing the valve seating 242 thereto. FIG. 12*c* depicts the last stage of deployment, when the over tube 60 (not seen in FIG. 12*c*) is totally pulled back allowing the second row of barbs 65'' to expand and the valve to expand to its full diameter 245. Alternatively, the attachment means may comprise adhesives, nits, magnets, hooks, pins, clips, staples, and the like. Additionally or alternatively, as shown in FIG. 11*b*, the attachment means may be an indent 63 or special profile.

Figure 13:
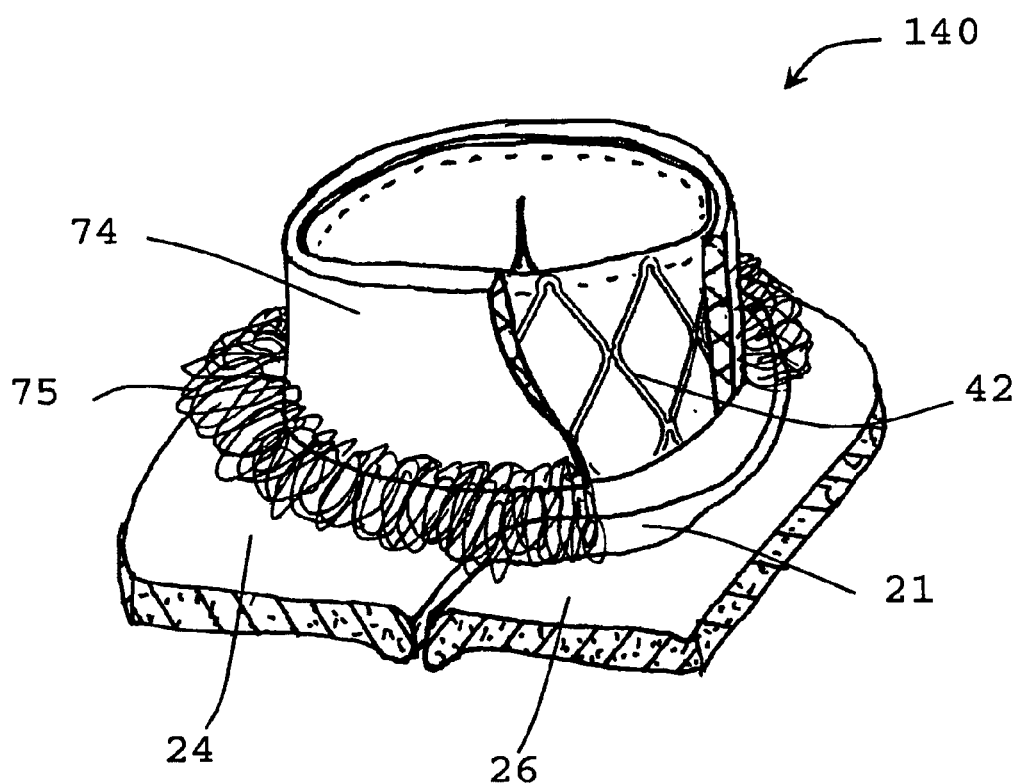
FIG. 13 represents a view of a mitral valve coated by a material which induces and accelerates tissue growth, according to further embodiments of the present invention.

With reference to FIG. 13 a textured surface and/or an artificial fabric 74, which coats the outer circumference of the prosthetic valve 140 and covers the valve seating 42 is shown. An additional portion of fabric 75 is suggested inducing and accelerates tissue growth and helps to secure the valve 140 into the implantation site, functioning in a manner similar to a mitral repair ring, preventing the heart wall from further expanding and assisting in the sealing of the native valve opening 21 and preventing mitral regurgitation. Optionally the circumference of the prosthetic valve seating includes markers which optimize positioning under fluoroscopy.

Figure 14:
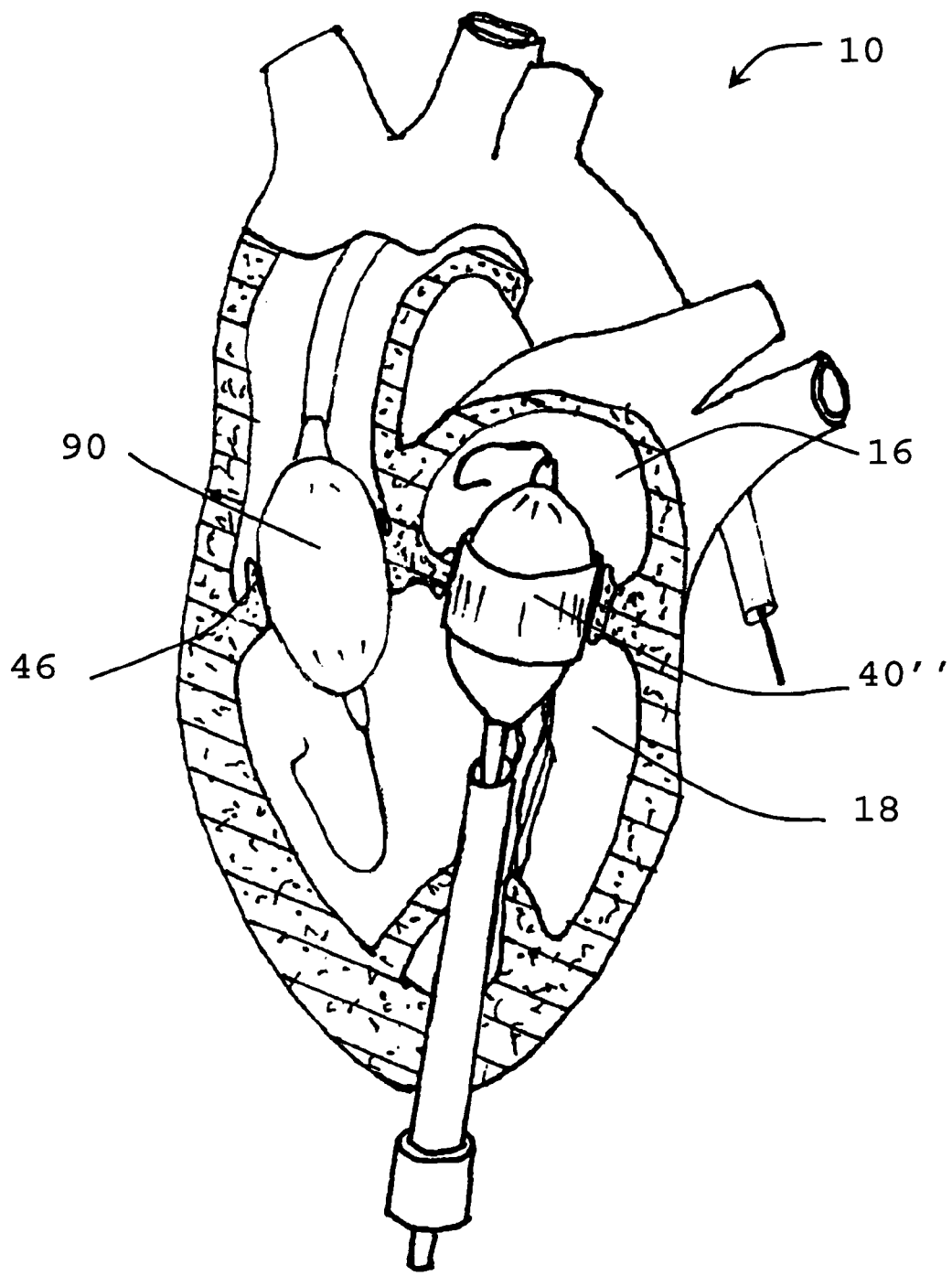
FIG. 14 illustrates a means of positioning the prosthetic mitral valve in the implant site according to another embodiment of the present invention.

Reference is now made to FIG. 14 which describes a solution to another core problem of positioning a prosthetic valve 40" within the beating heart 10. In order to be able to inflate a balloon which blocks the blood passage in the heart it is possible to temporarily stop the blood pressure by pacing the heart to a very high heart rate and thus causing very low blood pressure, or alternatively to apply drugs which temporarily stop the heart. In addition in order to preserve the correct heart geometry and prevent the aortic valve and annulus from collapsing, it is here suggested to inflate a balloon 90 inside the aortic valve 46, and only then to expand the mitral valve. This technique ensures preservation of the heart shape and geometry.

Novel surgical procedures are thus disclosed for implanting a prosthetic valve apparatus that may be as known in the art, which permits implantation thereof without major invasive surgical intervention, such as by using a catheter technique. These minimally invasive procedures and flexibility of methodology will generally make it possible for the patient to resume a substantially normal life. The methods may utilize a known prosthetic valve apparatus, such as one of those referenced hereinabove. Such valves are generally characterized by including a valve seating which is coupled to a one way valve for implantation in the body by means of a technique of catheterization.

The valve seating may be a type of stent which is a radially collapsible and re-expandable cylindrical tube or annular member or mesh sleeve. The collapsible one-way valve is permanently mounted on the valve seating by a suitable technique, such as gluing, welding or by means of a number of suitable sutures.

The valve seating may be comprised of a plurality of strut members having a three-dimensional cage-like structure for engaging the leaflet tissue around the aperture 36, into which the valve seating is inserted. When the valve apparatus is in an expanded configuration, the strut members expand so that the apparatus dynamically conforms to the size and shape of the novel orifice 36' and when the valve apparatus 40 is in its collapsed configuration the strut members are collapsed/folded. The mesh material of the valve seating allows it to compress longitudinally and remain radially crimped while still providing sufficient radial force rigidity such that the valve seating maintains its shape once it has been radially expanded to a desired size.

The expandable valve seating may be made from a biocompatible metallic or polymer material, or a metallic or polymer material that is suitably coated, impregnated, or otherwise treated with a material or combination of materials to impart biocompatibility. The expandable valve seating typically has a semi-rigid or flexible structure, and may be made of a flexible, resiliently yieldable material such as silicone, polytetrafluoroethylene (PTFE), expanded-PTFE (ePTFE), polyurethane, or other polymeric material. It may, however consist of stainless steel or cobalt chrome alloy.

In one embodiment, the expandable valve seating may be made from a super elastic, shape memory material such as Nitinol alloy which can be collapsed to a very small diameter and spring back to a large diameter adequate for a valve orifice cross-section, alternatively it may undergo a phase change as it approaches body temperature and thus reach the desired diameter, it being appreciated that both these characteristics may be combined. In other embodiments, a polymer material may be injected into a different, base material forming the expandable valve seating to impart desired stiffness, flexibility, resilience, or other properties.

Optionally, the expandable valve seating may include biodegradable materials such as biopolymers, thermoplastic starch, polyalctides, cellulose or aliphatic aromatic copolyesters. The expandable valve seating may also be made of a radio-opaque material and/or include radio-opaque markers to facilitate fluoroscopic visualization.

Moreover, the expandable valve seating may be at least partially treated with at least one therapeutic agent. Optionally, the therapeutic agent is eluted into the cardiac tissue or into the cardiac chamber over time. Available therapeutic agents are known to significantly reduce or even prevent a variety of pathological conditions including, but not limited to, arrhythmias, thrombosis, stenosis and inflammation. Accordingly, the therapeutic agent may include at least one of an anti-arrhythmic agent, anticoagulant, an antioxidant, a fibrinolytic, a steroid, an anti-apoptotic agent, and/or an anti-inflammatory agent. Optionally or additionally, the therapeutic agent may be capable of treating or preventing other disease or disease processes such as microbial infections and heart failure. In these instances, the therapeutic agent may include an inotropic agent, a chronotropic agent, an anti-microbial agent, and/or a biological agent such as a cell or protein. A plurality of portions of the present invention may each be separately treated with a different one of the preceding therapeutic agents or other suitable therapeutic agents.

The prosthetic one way valve that is appropriate for use with the present invention which is mounted on the prosthetic valve seating may be made from one or more pieces of biological material formed into a valve having at least one leaflet conduit having dimensions that correspond to the dimensions of the diseased mitral valve. The one-way valve in its open position allows flow to pass through the prosthetic valve from the inlet to the outlet, whereas a reverse flow is prevented due to the collapsible slack portions of the valve assembly that collapse inwardly to block the reverse flow Materials of biological origin (e.g., bovine, porcine, equine, ovis aries pericardial tissue) are typically used to construct one-way valves. Specific examples of such prosthetic heart valves are known in the art. The prosthetic one way valve is operatively secured to the expandable valve seating, such as by sutures. Alternatively, the prosthetic valve may be secured to the expandable valve seating in a variety of different manners including, for example, clips, pins, staples, and the like.

The methods of treatment described herein may be advantageous over known methods for a number of reasons. One advantage is that rupture of chordae tendineae may be avoided. In contradistinction to known methods of using prosthetic valves, the apparatus is not inserted via the native valve into the existing native opening. Rather, a new aperture is formed in the anterior leaflet. Another advantage is it offers a novel solution for mitral regurgitation by closing the native valve and creating a new orifice where a new replacement one way valve is implanted which seating is wedged tightly therein. Generally no need for positioning of an annuloplasty ring as preliminary experiments indicate that the new location and method of installation of the prosthetic valve provides enhanced securing in place with reduced risk of displacement over prior art positions and methods. Also there is no need for prior sizing of the apparatus thus rendering the method more cost effective. Thus the method of the present invention provides a solution to the problems of displacement, paravalvular leakage, regurgitation and dilation.

These methods are advantageous as many of the different and available prosthetic valves known in the art, designed for implantation in the body in conventional locations by catheterization may be used in the novel procedure and new location, irrespective of the size and shape of the native valve. Thus the choice of valve is determined by its functionality, cost and availability and is largely independent of the specific patient's heart shape and size.

From the above description of the invention, those skilled in the art will perceive improvements, changes and modifications. Although transvascular approaches are illustrated, the skilled artisan should appreciate that an open surgery approach may be used to replace a diseased cardiac valve by using this method. Any number of attachment means could be provided and configured to anchor in the novel orifice.

Features shown with some specific embodiments may be incorporated with other embodiments. Thus the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A method of treating a patient with regurgitation during systole due to a dysfunctional or diseased valve comprising the steps of:
    (A) piercing an aperture through a first leaflet of the valve;
    (B) advancing and positioning a collapsed prosthetic valve apparatus comprising a one-way valve mounted on an expandable seating, into the aperture;
    (C) expanding the expandable seating and forcing an outer edge of the first leaflet against an outer edge of a second leaflet, thereby preventing the natural separating of the first and second leaflets in systole by forcing the outer edges of the leaflets together and preventing their separation, thereby preventing regurgitation during systole; the prosthetic valve apparatus providing an alternative passageway for blood flow therethrough, whilst inhibiting back-flow in systole.

2. The method of claim 1, wherein said valve is a mitral valve.

3. The method of claim 2, wherein said first leaflet is an anterior leaflet.

4. The method of claim 2, wherein the first leaflet of the mitral valve is accessed via the left ventricle.

5. The method of claim 4, wherein said access is by a transvascular approach route.

6. The method of claim 4, wherein said access uses transcatheterization.

7. The method of claim 4, wherein the left ventricle is accessed transapically.

8. The method of claim 7, wherein said piercing is performed when the heart is in systole causing an anterior mitral valve leaflet to coapt with a posterior mitral leaflet.

9. The method of claim 4, wherein the left ventricle is accessed via the aortic valve.

10. The method of claim 9, wherein said piercing is performed when the heart is in systole causing the anterior mitral valve leaflet to coapt with the posterior mitral leaflet.

11. The method of claim 2, wherein the first leaflet of the mitral valve is accessed via right atrium by a transvascular approach.

12. The method of claim 11, using transcatheterization.

13. The method of claim 11, wherein the right atrium is accessed via vena cava and a left atrium is accessed by piercing septum interatrial.

14. The method of claim 1, wherein said piercing is by a technique selected from the group comprising mechanical tools, laser tools and hot wires.

15. The method of claim 1, wherein the expandable seating has at least one of the following limitations:
    (i) said expandable seating is an annular member and the step of expanding the expandable seating comprises inflating a balloon within the annular member; (ii) the expandable seating comprises a shape memory alloy that expands as it approaches body temperature; (iii) the expandable seating comprises a super elastic alloy that expands as it released from a constraining tube (over tube); (iv) the expandable seating is coated with a material which aids tissue growth; (v) the expandable seating has a textured surface which engages surrounding tissue to secure valve apparatus in place;
    (vi) the expandable seating comprises self-expanding shoulders which assist in securing the valve in its proper position.

16. The method of claim 1, comprising a preliminary step of obtaining regulatory approval for the prosthetic valve apparatus for insertion into the aperture made within the first leaflet of the valve.

17. The method of claim 1, comprising a preliminary step of packaging the prosthetic valve apparatus in a package labeled as appropriate for insertion into the aperture made within the first leaflet of the valve.

18. The method of claim 1, comprising a preliminary step of packaging the prosthetic valve apparatus with instructions describing its suitability for insertion into the aperture made within the first leaflet of the valve.

19. The method of claim 1, comprising a preliminary step of marketing the prosthetic valve apparatus for insertion into the aperture made within the first leaflet of the valve.

20. The method of claim 1, comprising a preliminary step of inflating a balloon in the aortic valve.

21. The method of claim 1, for treating mitral valve prolapse.

* * * * *